(12) United States Patent
Fields

(10) Patent No.: US 9,145,435 B2
(45) Date of Patent: Sep. 29, 2015

(54) UREA COMPOUNDS

(71) Applicant: Eli Lilly and Company, Indianapolis, IN (US)

(72) Inventor: Todd Fields, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/511,201

(22) Filed: Oct. 10, 2014

(65) Prior Publication Data

US 2015/0111846 A1    Apr. 23, 2015

Related U.S. Application Data

(60) Provisional application No. 61/891,995, filed on Oct. 17, 2013.

(51) Int. Cl.

| | |
|---|---|
| *C07H 19/044* | (2006.01) |
| *C07H 17/02* | (2006.01) |
| *A61K 31/438* | (2006.01) |
| *C07H 19/04* | (2006.01) |
| *C07D 487/10* | (2006.01) |

(52) U.S. Cl.
CPC .............. *C07H 17/02* (2013.01); *A61K 31/438* (2013.01); *C07D 487/10* (2013.01); *C07H 19/04* (2013.01); *C07H 19/044* (2013.01)

(58) Field of Classification Search
None
See application file for complete search history.

(56) References Cited

U.S. PATENT DOCUMENTS

| | | | |
|---|---|---|---|
| 7,851,167 B2 | 12/2010 | Xu | |
| 8,697,849 B2 | 4/2014 | Qu et al. | |
| 8,785,404 B2 * | 7/2014 | Qu .................................. | 514/27 |
| 2008/0139484 A1 * | 6/2008 | Teranishi et al. ............... | 514/25 |

FOREIGN PATENT DOCUMENTS

EP    1803729 A1    7/2007

OTHER PUBLICATIONS

Fushimi et al., "Design, synthesis, and structure—activity relationships of a series of 4-benzyl-5-isopropyl-1H-pyrazol-3-yl b-D-glycopyranosides substituted with novel hydrophilic groups as highly potent inhibitors of sodium glucose co-transporter 1 (SGLT1)" Bioorganic & Medicinal Chemistry 21 (2013) 748-765.
The International Search Report, PCT/US2014/060882, Nov. 26, 2014, Eli Lilly and Company.
The Written Opinion of the International Searching Authority, PCT/US2014/060882, Nov. 26, 2014.

* cited by examiner

*Primary Examiner* — Traviss C McIntosh, III
(74) *Attorney, Agent, or Firm* — Nelson L. Lentz

(57) ABSTRACT

The present invention provides a compound of Formula I:

Formula I or a pharmaceutically acceptable salt thereof.

6 Claims, No Drawings

UREA COMPOUNDS

The present invention relates to novel urea compounds, to pharmaceutical compositions comprising the compounds, to methods of using the compounds to treat physiological disorders, and to intermediates and processes useful in the synthesis of the compounds.

The present invention is in the field of treatment of diabetes and other diseases and disorders associated with hyperglycemia. Diabetes is a group of diseases that is characterized by high levels of blood glucose. It affects approximately 25 million people in the United States and is also the $7^{th}$ leading cause of death in U.S. according to the 2011 National Diabetes Fact Sheet (U.S. Department of Health and Human Services, Centers for Disease Control and Prevention). Sodium-coupled glucose cotransporters (SGLT's) are one of the transporters known to be responsible for the absorption of carbohydrates, such as glucose. More specifically, SGLT1 is responsible for the transport of glucose across the brush border membrane of the small intestine Inhibition of SGLT1 may result in reduced absorption of glucose in the small intestine, thus providing a useful approach to treating diabetes.

U.S. Patent Application Publication No. 2008/0139484 A1 discloses 1-(β-D-glycopyranosyl)-3-substituted nitrogen-containing heterocyclic compounds having SGLT1 and/or SGLT2 inhibitory activity which are further disclosed as being useful for the prevention or treatment of a disease associated with hyperglycemia, such as diabetes. In addition, U.S. Pat. No. 7,851,617 discloses indole deriviatives which are SGLT inhibitors and are further disclosed as being useful for treatment or prevention of diabetes and related conditions.

There is a need for alternative drugs and treatment for diabetes. The present invention provides certain novel inhibitors of SGLT1 which may be suitable for the treatment of diabetes.

Accordingly, the present invention provides a compound of Formula I:

Formula I

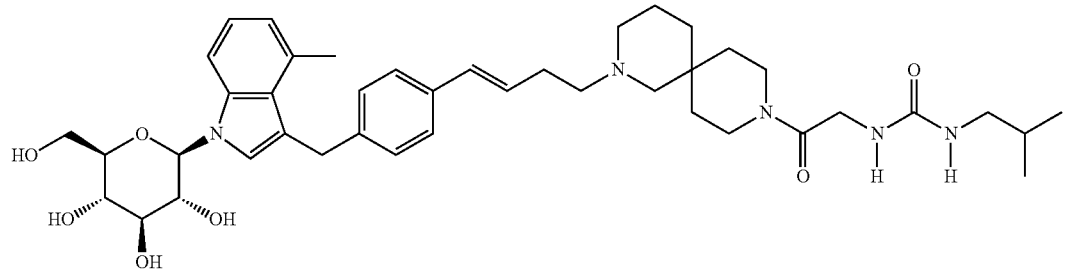

or a pharmaceutically acceptable salt thereof.

The present invention also provides a method of treating diabetes in a patient comprising administering to a patient in need of such treatment an effective amount of a compound of Formula I, or a pharmaceutically acceptable salt thereof. The present invention further provides a method of treating type 1 diabetes in a patient comprising administering to a patient in need of such treatment an effective amount of a compound of Formula I, or a pharmaceutically acceptable salt thereof. In addition, the present invention provides a method of treating type 2 diabetes in a patient comprising administering to a patient in need of such treatment an effective amount of a compound of Formula I, or a pharmaceutically acceptable salt thereof. The present invention also provides a method of treating impaired glucose tolerance (IGT), impaired fasting glucose (IFG), or metabolic syndrome in a patient comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy, in particular for the treatment of diabetes. In addition, this invention provides a compound of Formula I or a pharmaceutically acceptable salt thereof for use in the treatment of type 1 diabetes. In addition, this invention provides a compound of Formula I or a pharmaceutically acceptable salt thereof for use in the treatment of type 2 diabetes. This invention also provides the use of a compound of Formula I, or a pharmaceutically acceptable salt thereof, for the manufacture of a medicament for the treatment of diabetes. Furthermore, this invention provides the use of a compound of Formula I, or a pharmaceutically acceptable salt thereof, for the manufacture of a medicament for the treatment of type 1 diabetes. This invention also provides the use of a compound of Formula I, or a pharmaceutically acceptable salt thereof, for the manufacture of a medicament for the treatment of type 2 diabetes. The invention also provides the use of a compound of Formula I, or a pharmaceutically acceptable salt thereof, for the manufacture of a medicament for the treatment of IGT, IFG, or metabolic syndrome.

The invention further provides a pharmaceutical composition comprising a compound of Formula I, or a pharmaceutically acceptable salt thereof, with one or more pharmaceutically acceptable carriers, diluents, or excipients. This invention also encompasses novel intermediates and processes for the synthesis of the compound of Formula I.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition., Lippincott, Williams & Wilkins, 2006).

In a further aspect of the invention, the present compounds are administered in combination with one or more therapeutic agents, such as antidiabetic agents. Administration in combination includes simultaneous or sequential administration. In addition, simultaneous administration of the combination can be as a single combination dose or separate doses of each therapeutic agent. Examples of antidiabetic agents include metformin; a DPPIV inhibitor, such as sitagliptin or linagliptin; a sulfonylurea, such as glimepiride; a thiazolidinedione, such as pioglitazone; a basal insulin, such as glargine; a rapid acting insulin, such as HUMALOG or NOVOLOG; A GLP-1 agonist, such as exenatide or liraglutide; an SGLT2 inhibitor, such as dapagliflozin or empagliflozin; a glucagon receptor antagonist, such as LY2409021; and the like.

Compounds of Formula I are prepared as illustrated in the preparations, examples, and schemes below. The reagents and starting materials are readily available to one of ordinary skill in the art. All substituents, unless otherwise specified are as previously defined. It is understood that these schemes, preparations, and examples are not intended to be limiting to the scope of the invention in any way.

Examples of resolutions include selective crystallization techniques or chiral chromatography. (See, e.g. J. Jacques, et al., "Enantiomers, Racemates, and Resolutions", John Wiley and Sons, Inc., 1981, and E. L. Eliel and S. H. Wilen," Stereochemistry of Organic Compounds", Wiley-Interscience, 1994). It should be further clear to one of ordinary skill in the art that separation and isolation, by chromatography, chiral chromatography or selective crystallization, of individual diastereomers or geometric isomers of Formula I or individual diastereomers or geometric isomers of intermediates leading to Formula I, can occur at any convenient point in the synthesis.

As used herein, "δ? refers to part per million down-field from tetramethylsilane; "min" refers to minute or minutes; "hrs" refers to hours; "THF" refers to tetrahydrofuran; "EtOAc" refers to ethyl acetate; "MeOH" refers to methanol or methyl alcohol; "TFA" refers to trifluoroacetic acid; "DPPA" refers to diphenylphosphoryl azide; "HATU" refers to O-(7-azabenzotriazol-1-yl)-N,N,N',N'tetramethyluronium hexafluorophosphate; "CDI" refers to 1,1'-carbonyldiimidazole; "DDQ" refers to 2,3-dichloro-5,6-dicyano-1,4-benzoquinone "Xphos" refers to 2-dicyclohexylphosphino-2',4',6'-triisopropylbiphenyl; "MTBE" refers to methyl tert-butyl ether; "mins" refers to minutes; "HPLC" refers to high-performance liquid chromatography; "Ac" refers to an acetyl substituent of the following structure:

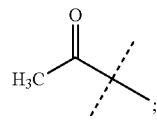

and the term "BOC" refers to a t-butyloxycarbonyl protecting group.

Pharmaceutically acceptable salts and common methodology for preparing them are well known in the art. See, e.g., Gould, P. L., "Salt selection for basic drugs," *International Journal of Pharmaceutics*, 33: 201-217 (1986); Bastin et al. "Salt Selection and Optimization Procedures for Pharmaceutical New Chemical Entities," *Organic Process Research and Development*, 4: 427-435 (2000); and S. M. Berge, et al., "Pharmaceutical Salts," Journal of Pharmaceutical Sciences, Vol. 66, No. 1, January 1977. One skilled in the art of synthesis will appreciate that the compounds of Formula I as amines are organic bases, and that they are readily converted to and isolated as pharmaceutically acceptable salts using techniques and conditions well known to one of ordinary skill in the art.

Scheme I

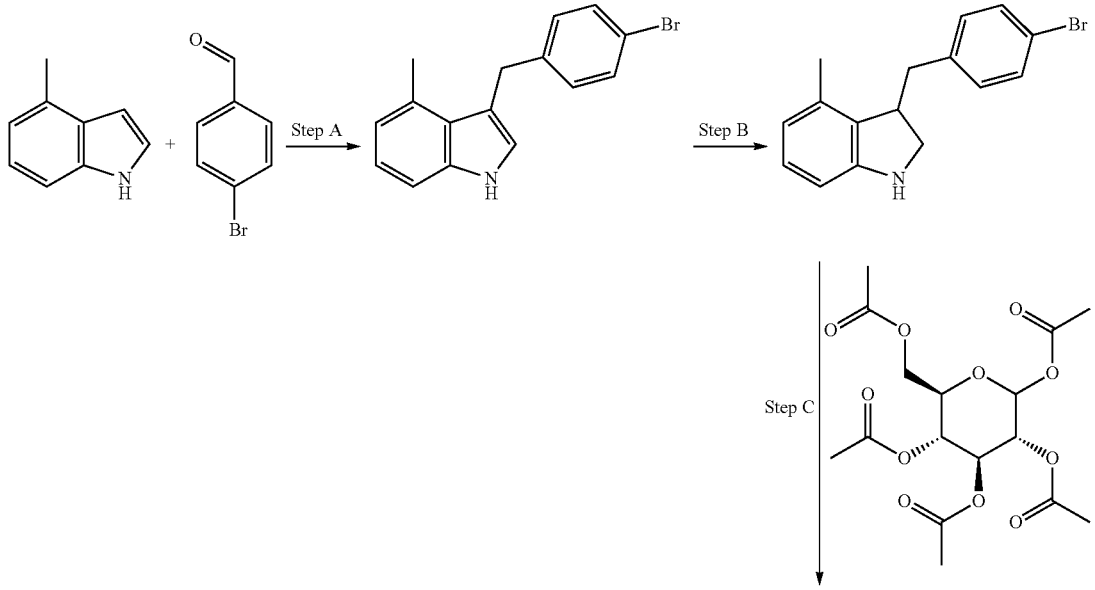

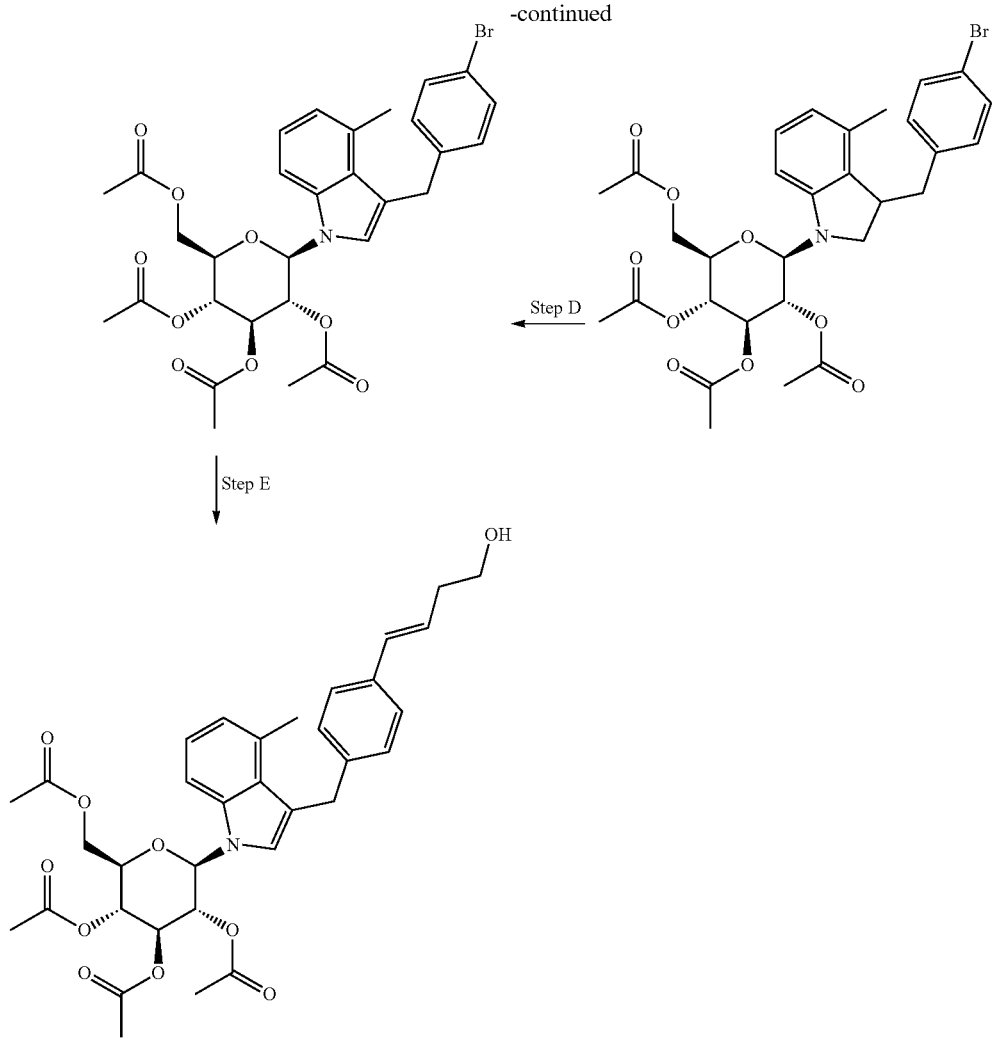

Preparation 1

3-[(4-bromophenyl)methyl]-4-methyl-1H-indole

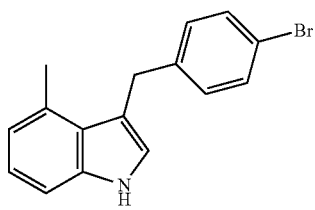 [SMILES: Cc1cccc2[nH]cc(Cc3ccc(Br)cc3)c12]

Scheme I, Step A: Add TFA (114.4 mmol) to a solution of 4-bromobenzaldehyde (76.2 mmol), 4-methylindole (76.2 mmol), and triethylsilane (228.4 mmol) in dichloromethane (10 mL) pre-cooled in an ice bath. Allow the mixture to warm to room temperature and stir for 2 hours. Add additional triethylsilane (228.4 mmol) and warm the mixture to 30° C. overnight in an oil bath. Dilute the reaction with water (100 mL) and extract with dichloromethane (2×100 mL). Separate and wash the organic phase with water (2×100 mL) and brine (100 mL). Dry the organic phase over sodium sulfate, filter, and concentrate under reduced pressure. Purify the residue by flash chromatography over silica gel (120 g cartridge) eluting with 0-10% ethyl acetate in petroleum ether to yield the title compound (8 g, 26.6 mmol): MS (m/z): 301 (M+1)

Preparation 2

3-[4-bromophenyl)methyl]-4-methyl-indoline

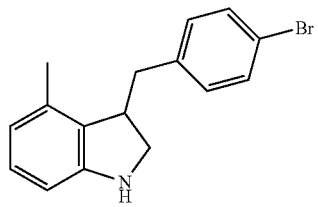 [SMILES: Cc1cccc2c1C(Cc1ccc(Br)cc1)CN2]

Scheme I, Step B: Add sodium cyanoborohydride (13.3 mmol) to a solution of 3-[(4-bromophenyl)methyl]-4-methyl-1H-indole (26.6 mmol) in acetic acid (20 mL) and stir at room temperature overnight. Dilute the reaction with water (200 mL) and add sodium bicarbonate until pH=6 is achieved. Extract with ethyl acetate (3×100 mL) and wash the combined organics with water (2×100 mL) and brine (100 mL). Dry the organics over sodium sulfate, filter, and concentrate under reduced pressure. Purify by flash chromatography (120 g silica gel cartridge) eluting with 0-15% ethyl acetate in petroleum ether to yield the title compound (2.2 g, 7.3 mmol): MS (m/z): 302 (M+1).

Preparation 3

[(2R,3R,4S,5R,6R)-3,4,5-triacetoxy-6-[3-[(4-bromophenyl)methyl]-4-methyl-indolin-1-yl]tetrahydropyran-2-yl]methyl acetate.

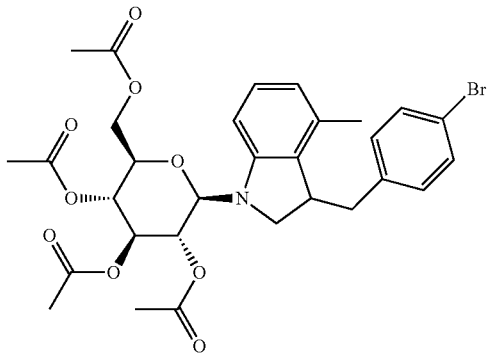 [SMILES: CC(=O)OC[C@H]1O[C@@H](N2CC(Cc3ccc(Br)cc3)c3c(C)cccc32)[C@H](OC(C)=O)[C@@H](OC(C)=O)[C@@H]1OC(C)=O]

Scheme I, Step C: Add [(2R,4S,5R,6S)-3,4,5,6-tetraacetoxytetrahydropyran-2-yl]methyl acetate (10.6 mmol) and 3-[(4-bromophenyl)methyl]-4-methyl-indoline (10.6 mmol) to a solution of acetic acid (69.8 mmol) in methanol (80 mL). Stir at room temperature overnight. Filter the reaction mixture through a glass frit and wash the filter cake with methanol (2×10 mL). Dry the filter cake under vacuum to yield the title compound (2.3g, 3.6 mmol): MS (m/z): 632 (M+H).

Preparation 4

[(2R,3R,4S,5R,6R)-3,4,5-triacetoxy-6-[3-[(4-bromophenyl)methyl]-4-methyl-indol-1-yl]tetrahydropyran-2-yl]methyl acetate

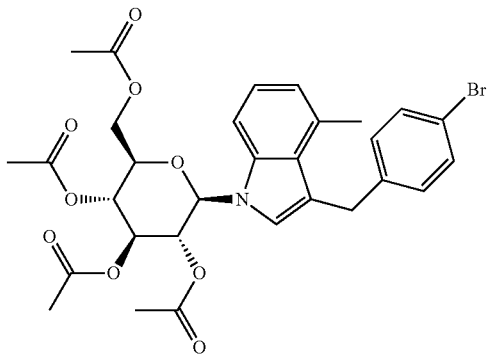 [SMILES: CC(=O)OC[C@H]1O[C@@H](n2cc(Cc3ccc(Br)cc3)c3c(C)cccc32)[C@H](OC(C)=O)[C@@H](OC(C)=O)[C@@H]1OC(C)=O]

Scheme I, Step D: Add manganese (IV) oxide (172.5 mmol) to a solution of [(2R,3R,4S,5R,6R)-3,4,5-triacetoxy-6-[3-[(4-bromophenyl)methyl]-4-methyl-indolin-1-yl]tetrahydropyran-2-yl]methyl acetate (5.85 mmol) in dichloromethane (20 mL). Stir at room temperature for 48 hours. Filter the reaction through diatomaceous earth and concentrate under reduced pressure. Treat the crude product with dichloromethane/methanol (30 mL of 10:1) and stir for 15 minutes. Filter the resulting precipitate and rinse the filter cake with methanol (2×10 mL). Dry the filter cake under vacuum to yield the title compound as a colorless solid (2.5 g 3.97 mmol): MS (m/z): 630 (M+H).

Preparation 5

[(2R,3R,4S,5R,6R)-3,4,5-triacetoxy-6-[3-[[4-[(E)-4-hydroxybut-1-enyl]phenyl]methyl]-4-methyl-indol-1-yl]tetrahydropyran-2-yl]methyl acetate

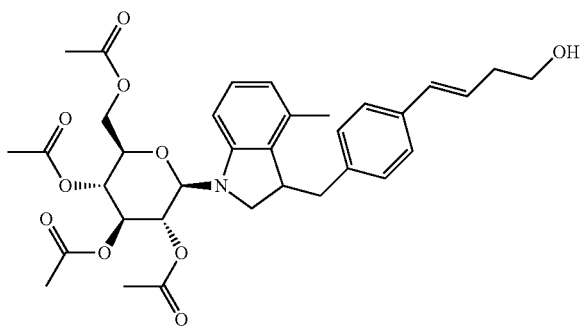 [SMILES: CC(=O)OC[C@H]1O[C@@H](N2CC(Cc3ccc(/C=C/CCO)cc3)c3c(C)cccc32)[C@H](OC(C)=O)[C@@H](OC(C)=O)[C@@H]1OC(C)=O]

Scheme I, Step E: Combine [(2R,3R,4S,5R,6R)-3,4,5-triacetoxy-6-[3-[(4-bromophenyl)methyl]-4-methyl-indol-1-yl]tetrahydropyran-2-yl]methyl acetate (1.67 mmol), 3-buten-1-ol (5 mmol), triethylamine (35.8 mmol), and acetonitrile (10 mL) and purge with nitrogen for 10 minutes. To this mixture add palladium acetate (0.17 mmol) and tri-o-tolylphosphine (0.33 mmol). Heat this mixture at 80° C. for 2 hours, then cool to room temperature. Dilute with ethyl acetate (50 mL) and water (50 mL). Separate and wash the organic phase with brine (50 mL). Dry the organics over sodium sulfate, filter, and concentrate under reduced pressure. Purify by flash chromatography (40 g silica gel cartridge) eluting with 5-80% ethyl acetate in dichloromethane to yield the title compound as a tan foam (0.8 g, 1.2 mmol): MS (m/z): 622.0 (M+H).

Scheme II
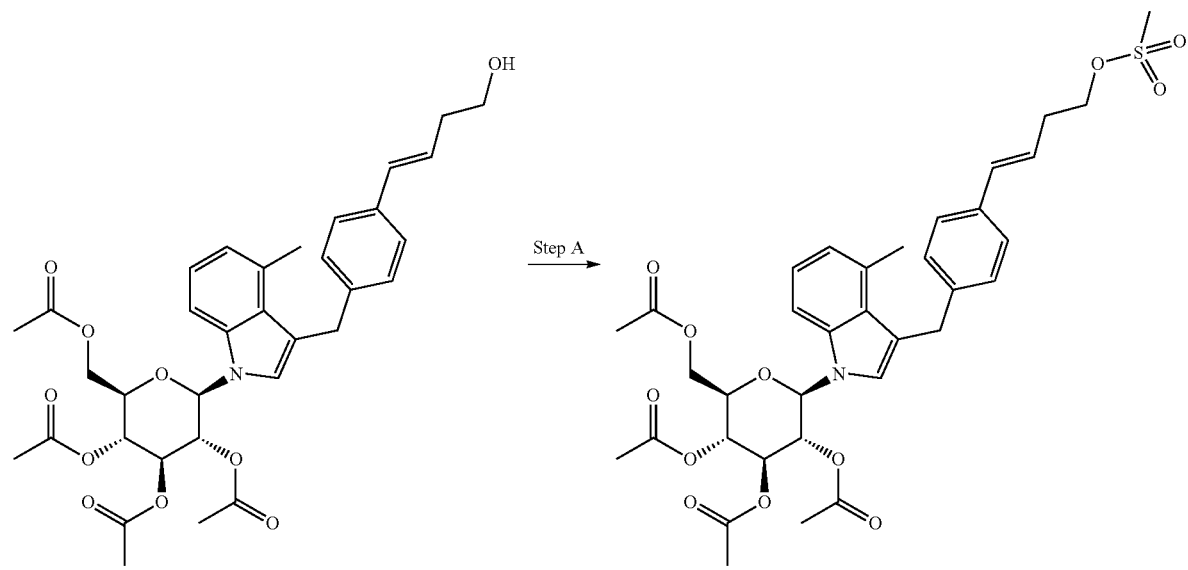
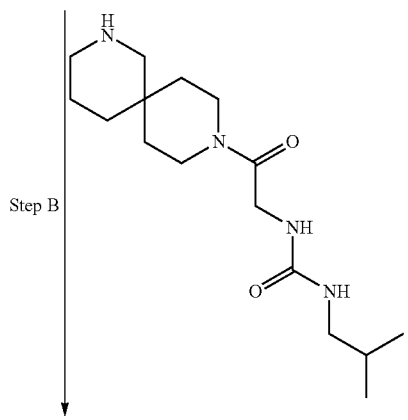
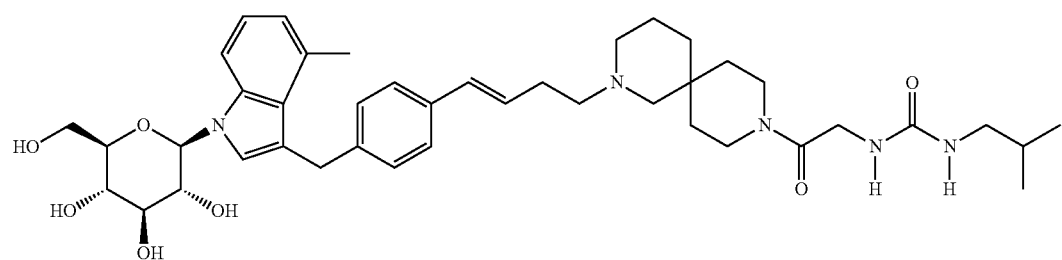
Formula I

Preparation 6

[(2R,3R,4S,5R,6R)-3,4,5-triacetoxy-6-[4-methyl-3-[[4-[(E)-4-methylsulfonyloxybut-1-enyl]phenyl]methyl]indol-1-yl]tetrahydropyran-2-yl]methyl acetate

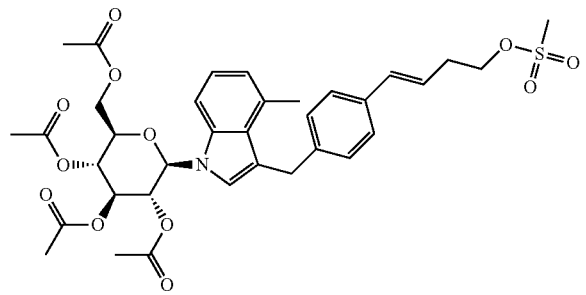 [SMILES: CC(=O)OC[C@H]1O[C@@H](n2cc(Cc3ccc(/C=C/CCOS(C)(=O)=O)cc3)c3c(C)cccc32)[C@H](OC(C)=O)[C@@H](OC(C)=O)[C@@H]1OC(C)=O]

Scheme II, Step A: To a solution of [(2R,3R,4S,5R,6R)-3,4,5-triacetoxy-6-[3-[[4-[(E)-4-hydroxybut-1-enyl]phenyl]methyl]-4-methyl-indol-1-yl]tetrahydropyran-2-yl]methyl acetate (1.2 mmol) in dichloromethane (50 mL) and triethylamine (3.6 mmol) at room temperature, add methanesulfonyl chloride (1.56 mmol) dropwise over 5 minutes. Stir at room temperature for 1 hour, then dilute the reaction with dichloromethane (100 mL). Wash the organics with water (2×100 mL) followed by brine (100 mL). Dry the organics over sodium sulfate, filter, and concentrate under reduced pressure to yield the title compound as a light yellow foam (0.84g, 1.2 mmol). Use this material in the next step (Scheme II, step B) without further purification.

Preparation 7

1-[2-(4,9-diazaspiro[5.5]undecan-9-yl)-2-oxo-ethyl]-3-isobutyl-urea

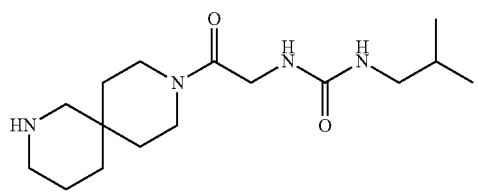 [SMILES: CC(C)CNC(=O)NCC(=O)N1CCC2(CCCNC2)CC1]

Preparation of benzyl 2-(isobutylcarbamoylamino)acetate

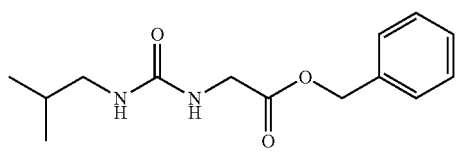 [SMILES: CC(C)CNC(=O)NCC(=O)OCc1ccccc1]

Charge 3-methylbutanoic acid (106.36 g), toluene (800 ml) and triethylamine (126.46 g) into a 3-neck flask (R1). Heat R1 to 90° C. Add a solution of DPPA (289.3 g) in toluene (400 ml) slowly (Care: N₂ released). Stir R1 at 90° C. for 30-60 mins, then cool to 20-30° C. In a separate flask (R2) charge benzyl 2-aminoacetate hydrochloride (200 g), triethylamine (150.54 g), and toluene (1000 ml) and stir at 20-30° C. for 1-2 hours. Add the R1 mixture into R2 drop wise slowly via addition funnel at 20-30° C. and stir for 1-2 hours. Slowly add the reaction mixture to water (2000 ml) with vigorous stirring. Separate the organic and extract the aqueous layer with EtOAc (2×1000 ml). Combine the organic layers and wash with 1 N hydrochloric acid (1000 ml), then 7% NaHCO₃ aq (1000 ml), then water (1000 ml), then 15% brine (1000 ml). Concentrate under reduced pressure. Slurry the residue with heptane (1000 ml) then filter the solid. Dry the filter cake under reduced pressure below 40° C. to give benzyl 2-(isobutylcarbamoylamino)acetate (218 g; 98.1% assay; 81.5% yield).

Preparation of 2-(isobutylcarbamoylamino)acetic acid

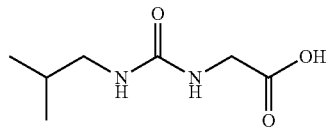

Charge benzyl 2-(isobutylcarbamoylamino)acetate (200 g; 98.1% assay), dry Pd/C (20 g; 10% w/w), and isopropyl alcohol (2000 ml) into an autoclave. Degas under vacuum and purge with hydrogen three times. Stir at 60° C. under 50-60 psi of H₂ for 4 hours. Cool the mixture to 20-30° C. and filter through diatomaceous earth and concentrate the filtrate under reduced pressure at 45-50° C. to 1-2 Vol. Add acetonitrile (1000 ml) and concentrate under reduced pressure at 45-50° C. to 2-3 Vol. Cool the mixture to 5-10° C. and filter. Dry the cake under reduced pressure at 45-50° C. to give of 2-(isobutylcarbamoylamino)acetic acid (112 g; 95.2% assay; 82.5% yield).

Preparation of Final Title Compound

To a round bottom flask add tert-butyl 4,9-diazaspiro[5.5]undecane-9-carboxylate hydrochloride (1.38 mmol), 2-(isobutylcarbamoylamino)acetic acid (1.15 mmol), dimethylformamide (3.8 mL), triethylamine (1.72 mmol), and HATU (1.26 mmol Stir at room temperature for 16 hours, then dilute with water (50 mL) and ethyl acetate (50 mL). Wash the organic phase with concentrated ammonium chloride (50 mL) and brine (50 mL). Dry the organics over sodium sulfate, filter, and concentrate under reduced pressure. Purify the intermediate by flash chromatography (40 g silica gel cartridge) eluting with 0-10% methanol in ethyl acetate to yield tert-butyl 9-12-(isobutylcarbamoylamino)acetyl[-4,9-diazaspiro[5.5]undecane-4-carboxylate (0.38 g, 0.93 mmol): MS (m/z): 411.2 (M+H).

To a solution of tert-butyl 9-[2-(isobutylcarbamoylamino)acetyl]-4,9-diazaspiro[5.5]undecane-4-carboxylate (0.38 g, 0.93 mmol) in 1,4-dioxane (1.75 mL), add 4M HCl in 1,4-dioxane (8.77 mmol). Stir the reaction at room temperature for 5 hours, then concentrate under reduced pressure. Purify the residue by dissolving in methanol and loading into a SCX (ion exchange) column. Rinse the loaded column with methanol (3×25 mL) then flush the column with 2N ammonia in methanol. Combine and concentrate the ammonia washes to yield the final title compound, 1-[2-(4,9-diazaspiro[5.5]undecan-9-yl)-2-oxo-ethyl]-3-isobutyl-urea (0.25 g, 0.81 mmol): MS (m/z): 311.0 (M+H).

Example 1a 1-isobutyl-3-[2-[4-[4-[(E)-4-[4-[[4-methyl-1-[(2R,3R,4S,5S,6R)-3,4,5-trihydroxy-6-(hydroxymethyl)tetrahydropyran-2-yl]indol-3-yl]methyl]phenyl]but-3-enyl]-4,9-diazaspiro[5.5]undecan-9-yl]-2-oxo-ethyl]urea

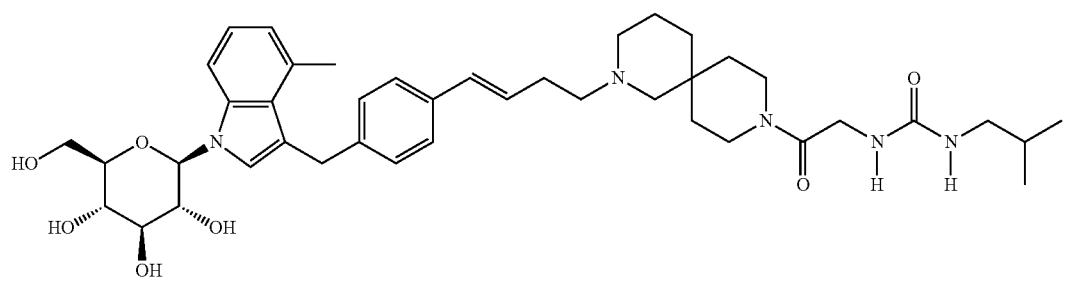 [SMILES: Cc1cccc2c1c(Cc1ccc(/C=C/CCN3CCCC4(CCN(C(=O)CNC(=O)NCC(C)C)CC4)C3)cc1)cn2[C@@H]1O[C@H](CO)[C@@H](O)[C@H](O)[C@H]1O]

Scheme II, Step B: To a solution of 1-[2-(4,9-diazaspiro[5.5]undecan-9-yl)-2-oxo-ethyl]-3-isobutyl-urea (0.21 mmol) in acetonitrile (2.5 mL), add [(2R,3R,4S,5R,6R)-3,4,5-triacetoxy-6-[4-methyl-3-[[4-[(E)-4-methylsulfonyloxy-but-1-enyl[phenyl]methyl]indol-1-yl]tetrahydropyran-2-yl]methyl acetate (0.17 mmol) followed by diisopropylethylamine (0.69 mmol). Heat the sealed reaction mixture at 80° C. for 16 hours. Concentrate the crude reaction under reduced pressure, then dissolve the crude intermediate in methanol (5 mL) and add sodium methoxide (0.53 mmol as a 30% solution in methanol). Stir at room temperature for 1 hour, then quench the reaction by adding a small piece of dry ice. Concentrate the crude reaction under reduced pressure. Purify by flash chromatography (120 g C18 column) eluting with 5-70% water (0.1% formic acid)/acetonitrile (0.1% formic acid). Combine the product containing fractions and concentrate under reduced pressure. Dissolve the product in water (50 mL) and neutralize the aqueous with concentrated sodium bicarbonate. Decant the aqueous phase and dissolve the remaining oil in dichloromethane/methanol (50 mL of 10:1). Dry the organics over sodium sulfate, filter, and concentrate under reduced pressure to yield the title compound as an off white foam (0.08 g, 0.63 mmol): MS (m/z): 746.5 (M+1).

Scheme III

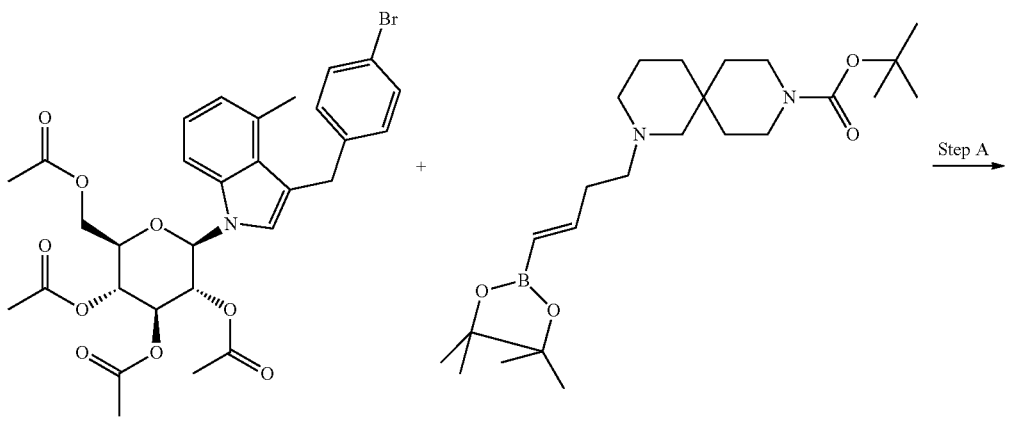

Step A

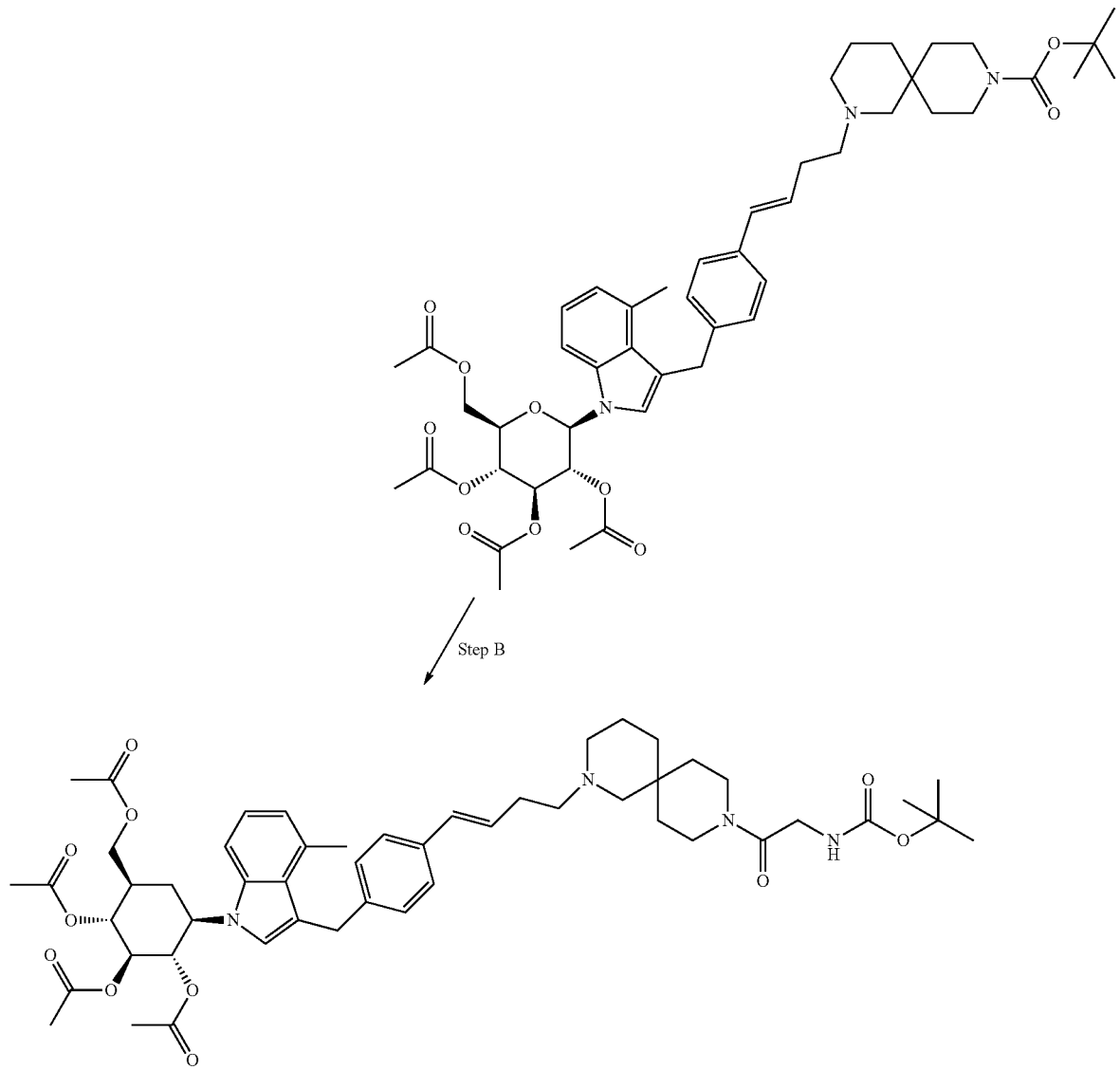

Preparation 9 tert-butyl 4-[(E)-4-(4,4,5,5-tetramethyl-1,3,2-dioxaborolan-2-yl)but-3-enyl]-4,9-diazaspiro[5.5]undecane-9-carboxylate

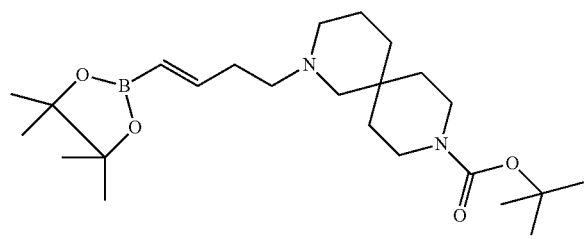 [SMILES: CC(C)(C)OC(=O)N1CCC2(CCCN(CC/C=C/B3OC(C)(C)C(C)(C)O3)C2)CC1]

Preparation of tert-butyl 4-(3-chloropropyl)-4-cyanopiperidine-1-carboxylate

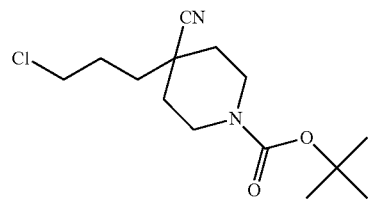 [SMILES: CC(C)(C)OC(=O)N1CCC(C#N)(CCCCl)CC1]

Charge 1780 g of THF and 86.6 g of diisopropylanmine to R1. Cool the mixture in R1 to −40° C.~−60° C. Add drop-wise 210.5 g of n-BuLi (1.6 eq) into R1 and stir the mixture for 0.5-1 hour. Charge 890 g of THF then 100.0 g of tert-butyl 4-cyanopiperidine-1-carboxylate into R2. Add the solution of tert-butyl 4-cyanopiperidine-1-carboxylate in R2 drop-wise to R1, controling the temperature at −40° C.~−60° C. Stir the mixture in R1 for 1~2 hour. Charge 890 g of THF and 130.5 g of 1-bromo-3-chloro-propane into R2. Add the solution of 1-bromo-3-chloro-propane in R2 drop-wise to R1, control the temperature at −40~−60° C. Stir the mixture in R1 for 3 hours at −40~−60° C. then slowly warm the mixture to 20~25° C. and stir for 13~16 hours. Cool the mixture to 0~5° C. Add drop-wise 525 g of NH₄Cl (saturated aqueous solution) then 500 g of water into R1. Concentrate the mixture to total weight 1000~1100 g below 40° C. then add 380 g of MTBE. Stir the mixture at 10~20° C. for 20-40 minutes then allow to stand for 30~60 mins Separate the aqueous layer and wash the organic layer with 2×500 g of H₂O. Concentrate the mixture to 300 g total weight below 50° C. Add 136 g of n-heptane then concentrate the mixture to 300 g total weight below 50° C. Cool the mixture 0-5° C., then add drop-wise 340 g of n-heptane. Stir the mixture in for 5~10 hours, then filter the suspension. Rinse the flask with 68.0 g of n-heptane, then wash the cake to provide of tert-butyl 4-(3-chloropropyl)-4-cyano-piperidine-1-carboxylate (118 g, 87.2% Assay, 75.4% yield): mass spectrum (m/z): 231 (M+H-tBu). Transfer the cake to a flask and add 610.0 g of Toluene. Concentrate mixture to 500 g total weight below 50° C. The product is stored as a toluene solution until required.

Preparation of tert-butyl 4,9-diazaspiro[5.5]undecane-9-carboxylate

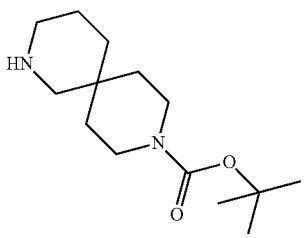 [SMILES: CC(C)(C)OC(=O)N1CCC2(CCCNC2)CC1]

Charge 435 g of toluene then 302.1 g of sodium bis(2-methoxyethoxy)aluminum hydride to R1. Cool the mixture to −5° C.~5° C. Charge 652.5 g of toluene and 50 g of tert-butyl 4-(3-chloropropyl)-4-cyano-piperidine-1-carboxylate into R2 and stir the mixture until clear. Add the solution of tert-butyl 4-(3-chloropropyl)-4-cyano-piperidine-1-carboxylate in R2 drop-wise to R1, control the temperature below 5° C. Stir the mixture in R1 for 0.5 hour at −5° C.~5° C. then warm the mixture to 15~20° C. and stir for 1~3 hours. Charge 25 g of sodium carbonate to R2 then add 1500 g of water and cool the mixture to 0~10° C. Add the mixture in R1 drop-wise to R2, controlling the temperature below 10° C. Warm the mixture to 20~40° C. and stir for 10-20 mins then allow to stand for 40-60 mins Separate the aqueous layer and wash the organic layer with 2×250 g water then 297.5 g of 25% aqueous sodium chloride solution. Concentrate the organic layer to 100 g total weight below 50° C. and then add 273.0 g of acetonitrile. Concentrate the organic layer to 250 g total weight below 50° C. of title compound, tert-butyl 4,9-diazaspiro[5.5]undecane-9-carboxylate, which is stored as a solution: mass spectrum (m/z): 255 (M+H).

Preparation of tert-butyl 4-but-3-ynyl-4,9-diazaspiro[5.5]undecane-9-carboxylate; oxalic acid

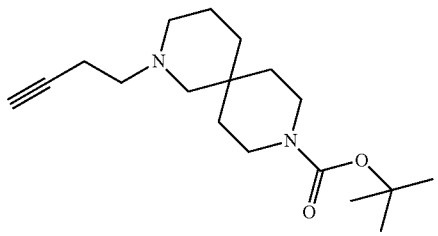

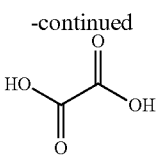

Charge in order, 23.7 g of CH₃CN, 10 g of tert-butyl 4,9-diazaspiro[5.5]undecane-9-carboxylate, 9.2 g of K₂CO₃ then 8.4 g of 4-bromobut-1-yne to R1. Heat the mixture to 65-70° C. and stir the mixture at 65-70° C. for 12-18 hours. Concentrate the mixture to a total weight of 30-40 g below 50° C., then add 76 g of MTBE and 50 g of water. Stir the mixture at 20-25° C. for 30 mins then allow to stand to 30 mins Separate the aqueous. Preopare a solution of 1 g of KOH in 49 g of water and add this to the organic layer at 20-25° C. Stir the mixture at 20-25° C. for 30 mins then allow to stand for 20-30 mins at 20-25° C. Separate the aqueous layer out and wash the organics with 50 g of water. Concentrate the organic phase to 40-50 g total weight below 50° C. in R1. Prepare a solution of 7.4 g of oxalic acid dihydrate in 39.5 g of acetone, then add drop wise the oxalic acid/acetone solution into R1 at 20-25° C. Stir the suspension at 20-25° C. for 2-3 hours then filter. Wash the cake with 15.2 g of MTBE. Slurry the cake in 89 g of THF and stir the mixture at 50° C. for 6-8 hours. Cool the mixture to 20-25° C. and filter. Wash the cake with 17.8 g of THF. Again, slurry the cake in 89 g of THF and stir the mixture at 50° C. for 6-8 hours. Cool the mixture to 20-25° C. and filter. Wash the cake with 17.8 g of THF. Dry the cake under vacuum at 50-60° C. for 16-18 hours to provide the title compound, tert-butyl 4-but-3-ynyl-4,9-diazaspiro[5.5]undecane-9-carboxylate; oxalic acid.

Preparation of Final Title Compound

Charge a 20 L vessel equipped with a bottom outlet valve with tert-butyl 4-but-3-ynyl-4,9-diazaspiro[5.5]undecane-9-carboxylate; oxalic acid (2.56 moles; 1.02 kg), potassium hydroxide (10% w/w aqueous solution; 7.69 moles; 4.31 kg) and MTBE (34.19 moles; 4.06 L; 3.01 kg). Stir the mixture until two clear phases form. Remove the organic layer and extract the aqueous layer with MTBE (1.5L). Combine the organic layers and wash with water (4L) then saturated aqueous sodium chloride solution (4L) and concentrate under reduced pressure. Add toluene (2L) to the residue and concentrate under reduced pressure. Again add toluene (2L) to the residue and concentrate under reduced pressure to give tert-butyl 8-but-3-ynyl-3,8-diazaspiro[5.5]undecane-3-carboxylate (787g; contains about 2% w/w toluene; 98% yield)

To a mixture of tert-butyl 8-but-3-ynyl-3,8-diazaspiro[5.5] undecane-3-carboxylate (2.41 moles; 750.86 g), zirconocene chloride (240.73 mmoles; 62.08 g), triethylamine (240.73 mmoles; 33.55 mL; 24.36 g), and 2-methyltetrahydrofuran (738 mL), add 4,4,5,5-tetramethyl-1,3,2-dioxaborolane (2.53 moles; 323.49 g). Heat the mixture to 60° C. and stir overnight. Cool the mixture and pass through a plug of silica eluting with dichloromethane. Concentrate the filtrate under reduced pressure to give the final title compound, tert-butyl 4-[(E)-4-(4,4,5,5-tetramethyl-1,3,2-dioxaborolan-2-yl)but-3-enyl]-4,9-diazaspiro[5.5]undecane-9-carboxylate (1072 g, about 94% purity, 96% yield).

Alternative Preparation of Final Title Compound

Add tert-butyl 4,9-diazaspiro[5.5]undecane-9-carboxylate hydrochloride (46.07 mmol) and cesium carbonate (115.2 mmol) to a solution of acetonitrile (200 mL). After stirring at room temperature for 20 minutes, add 4-bromobutyne (69.1 mmol) and heat the mixture to reflux with stirring overnight. Cool to room temperature and dilute with ethyl acetate (200 mL). Filter the reaction through a glass frit rinsing with ethyl acetate (2×100 mL). Concentrate the crude mixture under reduced pressure, then add ethyl acetate (200 mL) and wash the organics with water (200 mL) and brine (200 mL). Dry the organics over sodium sulfate, filter, and concentrate under reduced pressure to yield crude tert-butyl 4-but-3-ynyl-4,9-diazaspiro[5.5]undecane-9-carboxylate (13.6 g, 44.4 mmol): MS (m/z): 307.2 (M+H). To a round bottom flask under nitrogen, add tert-butyl 4-but-3-ynyl-4,9-diazaspiro[5.5]undecane-9-carboxylate (44.4 mmol), triethylamine (4.44 mmol), zirconocene chloride (4.44 mmol), and 4,4,5,5-tetramethyl-1,3,2-dioxaborolane (48.8 mmol). Heat this mixture to 60° C. for 3 hours, then stir overnight at room temperature. Dissolve the mixture in dichloromethane (20 mL) and purify by flash chromatography (330 g silica gel cartridge) eluting with 15-85% ethyl acetate in hexanes to yield the final title compound, tert-butyl 4-[(E)-4-(4,4,5,5-tetramethyl-1,3,2-dioxaborolan-2-yl)but-3-enyl]-4,9-diazaspiro[5.5]undecane-9-carboxylate (29.9 mmol) as a light yellow oil: MS (m/z): 435.2 (M+H).

Preparation 10 tert-butyl 4-RE)-4-[4-[[4-methyl-1-R2R,3R,4S,5R,6R)-3,4,5-triacetoxy-6-(acetoxymethyl)tetrahydropyran-2-yl]indol-3-yl]methyl]phenyl]but-3-enyl]-4,9-diazaspiro[5.5]undecane-9-carboxylate

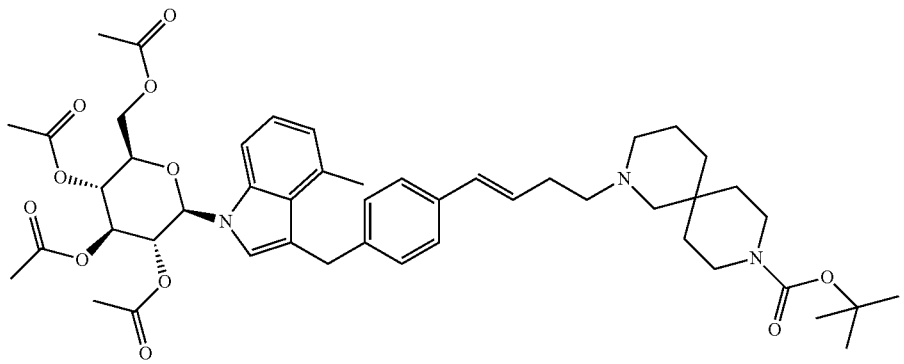 [SMILES: CC(=O)OC[C@H]1O[C@@H](n2cc(Cc3ccc(/C=C/CCN4CCCC5(CCN(C(=O)OC(C)(C)C)CC5)C4)cc3)c3c(C)cccc32)[C@H](OC(C)=O)[C@@H](OC(C)=O)[C@@H]1OC(C)=O]

Scheme III, Step A: Add R2R,3R,4S,5R,6R)-3,4,5-triacetoxy-6-[3-[(4-bromophenyl)methyl]-4-methyl-indol-1-yl]tetrahydropyran-2-yl]methyl acetate (27.8 mmol), tert-butyl 4-[(E)-4-(4,4,5,5-tetramethyl-1,3,2-dioxaborolan-2-yl)but-3-enyl]-4,9-diazaspiro[5.5]undecane-9-carboxylate (29.9 mmol), and potassium carbonate (83.3 mmol) to a solution of THF (150 mL) and water (20 mL). Purge the solution with nitrogen, then add palladium acetate (1.1 mmol) and Xphos (1.1 mmol). Heat the mixture to 65° C. for 16 hours. Cool to room temperature and dilute with ethyl acetate (200 mL) and water (200 mL). Separate and wash the organic phase with water (200 mL) and brine (200 mL). Dry the organics over sodium sulfate, filter, and concentrate under reduced pressure. Purify the residue by flash chromatography (330g silica gel cartridge) eluting with 10-100% ethyl acetate in dichloromethane to yield the title compound (19.4 g, 22.6 mmol): MS (m/z): 858.0 (M+H).

Preparation 11

[(2R,3R,4S,5R,6R)-3,4,5-triacetoxy-6-[3-[[4-[(E)-4-[9-[2-(tert-butoxycarbonylamino)acetyl]-4,9-diazaspiro[5.5]undecan-4-yl]but-1-enyl]phenyl]methyl]-4-methyl-indol-1-yl]tetrahydropyran-2-yl]methyl acetate

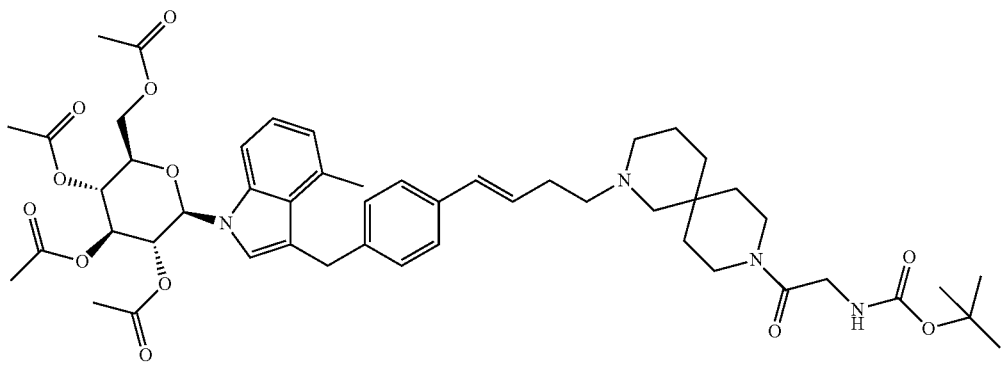 [SMILES: CC(=O)OC[C@H]1O[C@@H](n2cc(Cc3ccc(/C=C/CCN4CCCC5(CCN(C(=O)CNC(=O)OC(C)(C)C)CC5)C4)cc3)c3c(C)cccc32)[C@H](OC(C)=O)[C@@H](OC(C)=O)[C@@H]1OC(C)=O]

Scheme III, Step B: Add 4N HCl in 1,4-dioxane (112 5 mmol) to a solution of tert-butyl 4-[(E)-4-[4-[[4-methyl-1-[(2R,3R,4S,5R,6R)-3,4,5-triacetoxy-6-(acetoxymethyl)tetrahydropyran-2-yl]indol-3-yl]methyl]phenyl]but-3-enyl]-4,9-diazaspiro[5.5]undecane-9-carboxylate (22.5 mmol) in dichloromethane (200 mL) at room temperature. Stir for 3 hours, then concentrate under reduced pressure to yield crude [(2R,3R,4S,5R,6R)-3,4,5-triacetoxy-6-[3-[[4-[(E)-4-(4,9-diazaspiro[5.5]undecan-4-yl)but-1-enyl]phenyl]methyl]-4-methyl-indol-1-yl]tetrahydropyran-2-yl]methyl acetate dihydrochloride (22.5 mmol): MS (m/z): 758.0 (M+H). Add triethylamine (112 5 mmol) to a solution of [(2R,3R,4S,5R,6R)-3,4,5-triacetoxy-6-[3-[[4-[(E)-4-(4,9-diazaspiro[5.5]undecan-4-yl)but-1-enyl]phenyl]methyl]-4-methyl-indol-1-yl]tetrahydropyran-2-yl]methyl acetate dihydrochloride (22 5 mmol) in dichloromethane (200 mL). In a separate flask, add CDI (28.1 mmol) portion wise to a solution of 2-(tert-butoxycarbonylamino)acetic acid (27 mmol) in dichloromethane (50 mL). After stirring for 45 minutes at room temperature, add the solution to the previously prepared amine solution and stir at room temperature for 1 hour. Wash with a concentrated sodium bicarbonate solution (200 mL) and brine (200 ml). Dry the organics over sodium sulfate, filter, and concentrate under reduced pressure to yield crude title compound (21.6 g, 22.5 mmol): MS (m/z): 915.2 (M+H).

Scheme IV

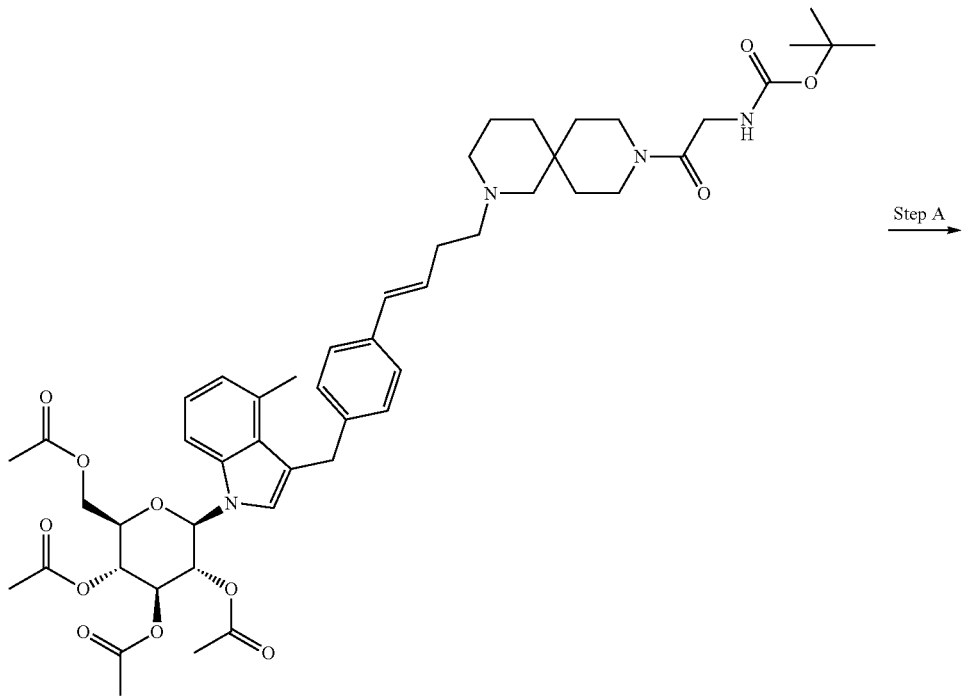

Step A

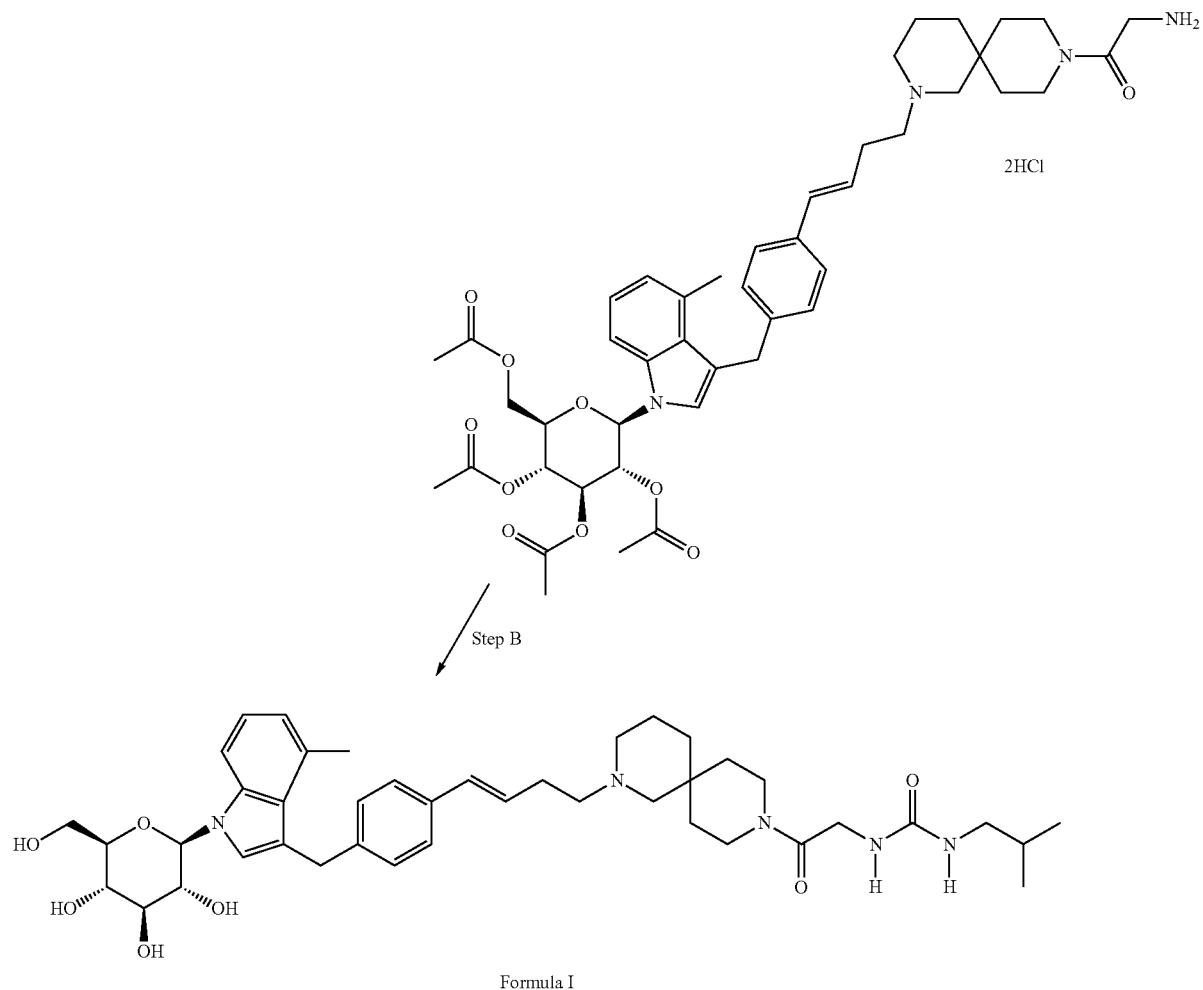

Formula I

Preparation 12

R2R,3R,4S,5R,6R)-3,4,5-triacetoxy-6-[3-[[4-[(E)-4-[9-(2-aminoacetyl)-4,9-diazaspiro[5.5]undecan-4-yl]but-1-enyl]phenyl]methyl]-4-methyl-indol-1-yl]tetrahydropyran-2-yl]methyl acetate dihydrochloride Scheme IV, Step A: Add 4N HCl 1,4-dioxane (113.3 mmol) to a solution of crude [(2R,3R,4S,5R,6R)-3,4,5-triacetoxy-6-[3-[[4-(E)-4-[9-[2-(tert-butoxycarbonylamino)acetyl]-4,9-diazaspiro[5.5]undecan-4-yl]but-1-enyl]phenyl]methyl]-4-methyl-indol-1-yl]tetrahydropyran-2-yl]methyl acetate (22.5 mmol) in dichloromethane (200 mL). Stir at room temperature for 4.5 hours, then concentrate under reduced pressure to yield crude title compound (22.6 g, 22 5 mmol) as a tan solid: MS (m/z): 815.2 (M+H).

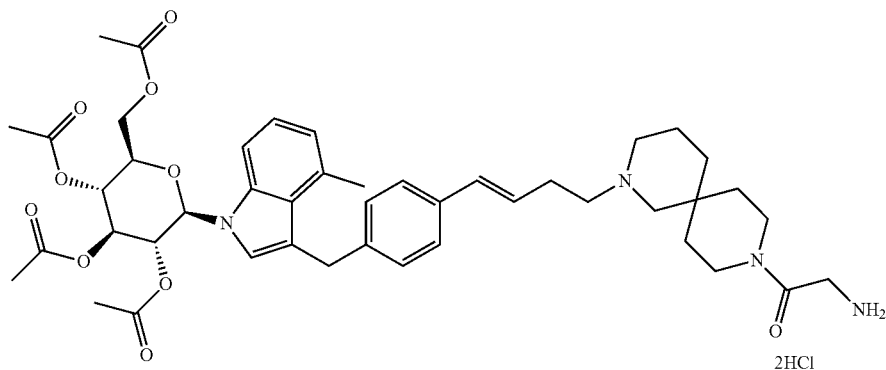 [SMILES: CC(=O)OC[C@H]1O[C@@H](n2cc(Cc3ccc(/C=C/CCN4CCCC5(CCN(C(=O)CN)CC5)C4)cc3)c3c(C)cccc32)[C@H](OC(C)=O)[C@@H](OC(C)=O)[C@@H]1OC(C)=O]

Example 1b

Alternative synthesis of 1-isobutyl-3-[2-[4-[(E)-4-[4-[[4-methyl-1-[(2R,3R,4S,5S,6R)-3,4,5-trihydroxy-6-(hydroxymethyl)tetrahydropyran-2-yl]indol-3-yl]methyl]phenyl]but-3-enyl[-4,9-diazaspiro[5.5]undecan-9-yl[-2-oxo-ethyl]urea

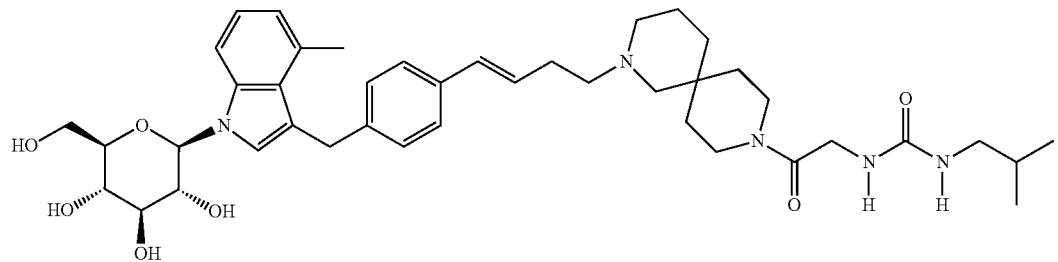 [SMILES: Cc1cccc2c1c(Cc1ccc(/C=C/CCN3CCCC4(CCN(C(=O)CNC(=O)NCC(C)C)CC4)C3)cc1)cn2[C@@H]1O[C@H](CO)[C@@H](O)[C@H](O)[C@H]1O]

Scheme IV, Step B: Add isobutyl isocyanate (30.6 mmol) to a solution of [(2R,3R,4S,5R,6R)-3,4,5-triacetoxy-6-[3-[[4-(E)-4-[9-(2-aminoacetyl)-4,9-diazaspiro[5.5]undecan-4-yl]but-1-enyl]phenyl]methyl]-4-methyl-indol-1-yl]tetrahydropyran-2-yl]methyl acetate dihydrochloride (22.5 mmol) and diisopropylethylamine (113.3 mmol) in dichloromethane (300 mL) and cool to 0° C. Warm to room temperature and stir for 2 hours. Dilute with water (200 mL) and separate the organic phase. Wash the organic phase with brine (200 mL). Dry over sodium sulfate, filter, and concentrate under reduced pressure. Add methanol (100 mL) and sodium methoxide (11.3 mmol). Stir at room temperature for 16 hours, then quench by adding a small piece of dry ice. Concentrate under reduced pressure. Purify by flash chromatography (400 g C18 cartridge) eluting with 5-80% acetonitrile (0.1% formic acid) in water (0.1% formic acid) in three portions. Concentrate under reduced pressure to yield the title compound (13.4 g, 18 mmol) as a formic acid salt containing small impurities. Dissolve the salt (12g) in water (500 mL). Neutralize the solution with a concentrated sodium bicarbonate solution. Collect the resulting precipitate on a glass frit and rinse with water (2×100 mL). Purify by flash chromatography (330 g silica gel cartridge) eluting with 15% methanol in dichloromethane. Concentrate the product fractions under reduced pressure to yield the title compound (8.8 g, 11.8 mmol): MS (m/z): 746.6 (M+H). H1 NMR (400.31 MHz, DMSO-d6): δ 7.29 (d, J=8.0 Hz, 1H), 7.22 (d, J=8.0 Hz, 2H), 7.07 (s, 1H), 7.06 (d, J=8.4 Hz, 2H), 6.93 (t, J=7.2 Hz, 1H), 6.65 (d, J=7.2 Hz, 1H), 6.35 (d, J=16.0 Hz, 1H), 6.26 (t, J=6.0 Hz, 1H), 6.15 (dt, J=16.0, 6.4 Hz, 1H), 5.88 (t, J=5.6 Hz, 1H), 5.29 (d, J=9.2 Hz, 1H), 5.09 (dd, J=11.6, 6.0 Hz, 2H), 5.01 (d, J=5.2 Hz, 1H), 4.47 (t, 5.6 Hz, 1H), 4.13 (bs, 2H), 3.78 (d, J =4.8 Hz, 2H), 3.63 (m, 2H), 3.59-3.15 (m, 11H), 3.12 (d, 5.2 Hz, 1H), 2.76 (t, J=6.4 Hz, 2H), 2.35 (s, 3H), 2.34-2.08 (m, 9H), 1.61-1.17 (m, 10H). 0.78 (d, J=6.8 Hz, 6H)

Scheme V

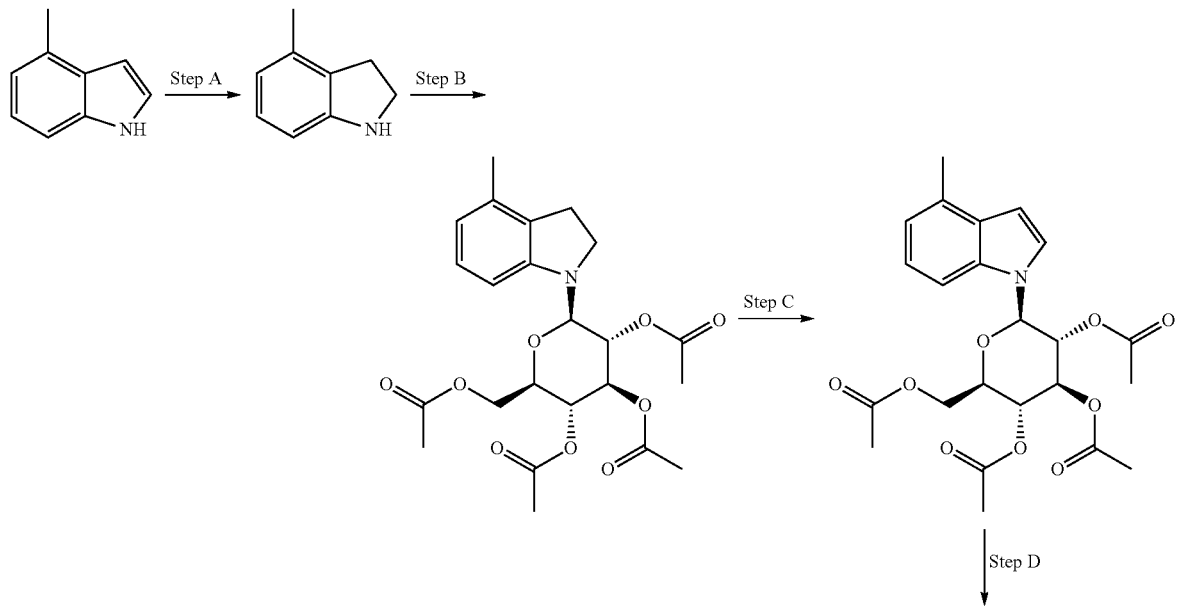

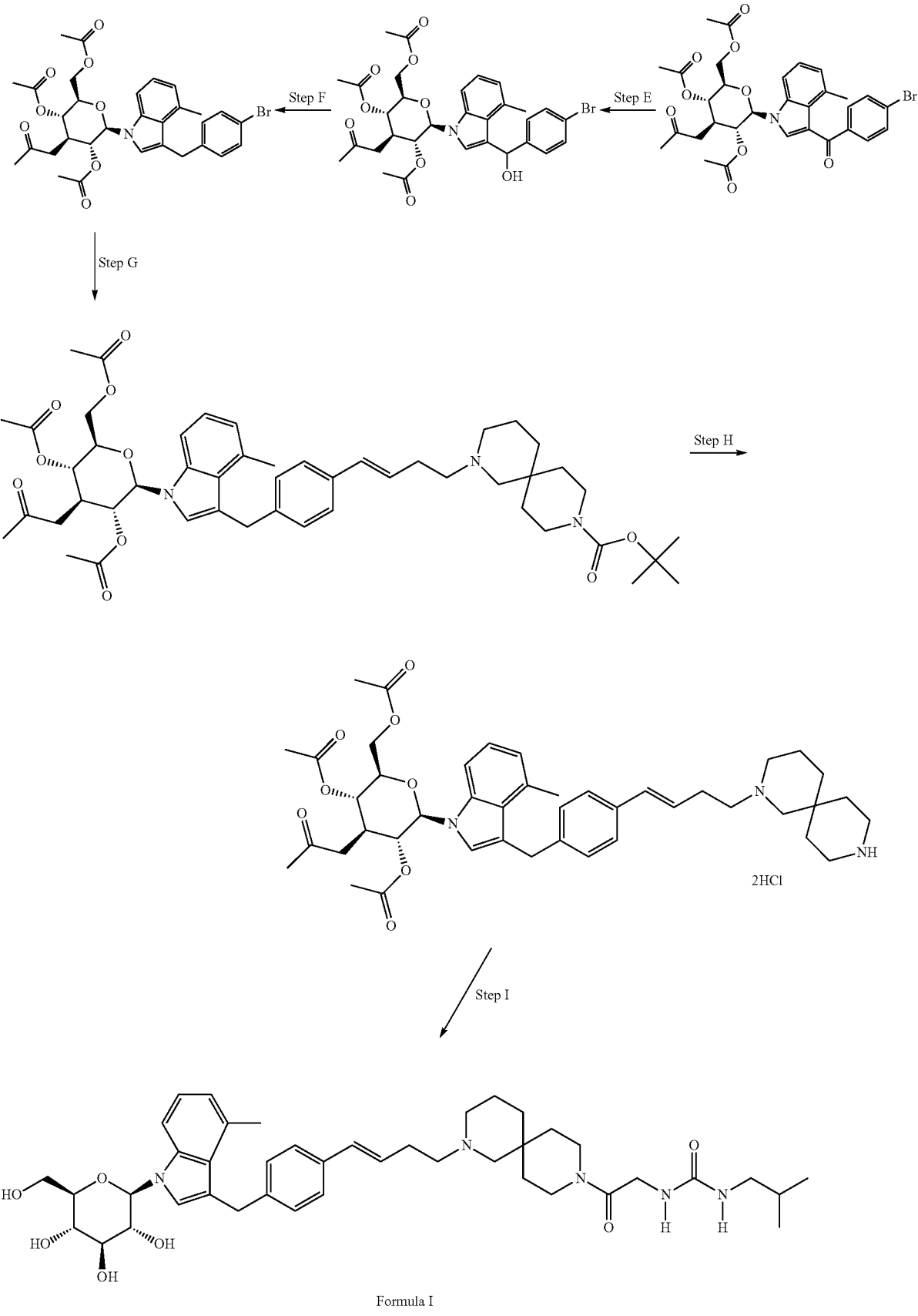
-continued
Formula I

Preparation 13

4-methylindoline

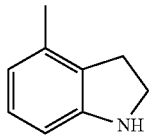

Method A

Scheme V, Step A: Charge 4-methyl-1H-indole (500 g; 1.0 equiv; 3.811 moles) and acetic acid (2000 mL) to a 20 L flask at room temperature. Cool the solution to 0° C. (internal temperature) and then add sodium cyanoborohydride (359.2 g; 1.5 equiv; 5.71 moles) in 5 equal portions, while not allowing the reaction mixture to warm above 10° C. When the addition is complete, stir the reaction mixture at room temperature for 2 hours. Cool the reaction mixture to 0° C. and add ice (5 Kg). Add a pre-cooled (5° C.) solution of sodium hydroxide (4M) very slowly to achieve a reaction mixture pH of 14. Extract the reaction mixture with ethyl acetate (2×10 L). Combine the organic layers and wash with water (1×10 L) and brine (1×10 L). Dry over anhydrous sodium sulfate, filter, and concentrate under reduced pressure to obtain the title compound (460 g, 90% yield): mass spectrum (m/z): 134 (M+1).

Method B

Scheme V, Step A: Charge trifluoroacetic acid (7.62 moles; 576.42 mL) to a 2000 mL 3 necked flask, equipped with thermometer, magnetic stirrer, nitrogen line, and dropping funnel. Place the flask in an ice/water bath and cool the mixture to 13° C. (internal temperature). Add 4-methyl-1H-indole (762.33 mmoles; 94.25 mL; 100.00 g) over 3 minutes not allowing the temperature of the reaction mixture to exceed 25° C. Stir the mixture for about 1 minute after the addition is complete, allowing the temperature of the reaction mixture to reach 20° C., then remove the flask from the ice bath and stir for 10 minutes at 20° C. Add triethylsilane (876.68 mmoles; 140.47 mL; 101.94 g) dropwise to the reaction over 41 minutes, allowing the temperature to rise to 25° C., then maintaining the temperature between 25° C. and 30° C. by use of a cool water bath as required. When the addition is complete stir the reaction mixture for 80 minutes. Cool the reaction mixture to 10° C. then pour into a mixture of ice (1000 g) 5M hydrochloric acid (800 ml) and MTBE (2000 ml) with stirring. Note that it is important to quench into a biphasic system to prevent the formation of impurities. Separate the aqueous phase and extract the organics with hydrochloric acid (400 ml; 2 M), then hydrochloric acid (2×200 ml; 2 M). Combine the aqueous extracts and cool in ice water. Add 50% w/w NaOH to achieve pH>10 keeping the temperature below 30° C. Extract the aqueous mixture with MTBE (1000 ml, then 200 ml). Combine the organic extracts, dry over anhydrous sodium sulfate, filter, and concentrate under reduced pressure to give the title compound (73 g; 68% yield): mass spectrum (m/z): 134 (M+1).

Method C

Scheme V, Step A: Add a solution of 4-methyl-1H-indole, (114.35 mmoles; 15.00 g) in tetrahydrofuran (75.00 mL) to a solution of p-toluenesulfonic acid monohydrate (137.22 mmoles; 23.63 g) in water (75.00 mL) with stirring at room temperature. Add 5% platinum on carbon (Johnson Matthey Type 103; 1.50 g) under a blanket of carbon dioxide. Place the mixture under an atmosphere of hydrogen (4.2 bar) and shake at room temperature overnight. Dilute the reaction mixture with sodium hydroxide (2M aqueous solution; 148.65 mmoles; 74.33 mL) and stir with MTBE (150.00 mL). Filter the mix through diatomaceous earth and wash the pad with MTBE (50 mL). Separate the filtrate and extract the aqueous with MTBE (100 mL). Combine the organics, dry over anhydrous magnesium sulfate, filter, and concentrate under reduced pressure to give the title compound (14.80 g; 97.17% yield): mass spectrum (m/z): 134 (M+1).

Preparation 14

[(2R,3R,4S,5R,6R)-3,4,5-triacetoxy-6-(4-methylindolin-1-yl)tetrahydropyran-2-yl]methyl acetate

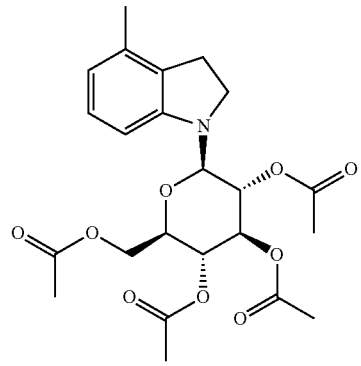 [SMILES: CC(=O)OC[C@H]1O[C@@H](N2CCc3c(C)cccc32)[C@H](OC(C)=O)[C@@H](OC(C)=O)[C@@H]1OC(C)=O]

Method A

Scheme V, Step B: Charge to a 20 L three neck flask a solution of 4-methylindoline (1000 g; 7.51moles) in ethanol:water (8000 ml: 1000 ml) and D-glucose (1480g; 8.25 moles). Heat the mixture for 6 hours at 80° C. Concentrate the mixture under reduced pressure and dissolve the residue in pyridine : dichloromethane (8000 ml: 8000 ml). Add dimethylaminopyridine (91.79 g; 0.75 moles) and cool the reaction mixture to 10° C. (internal temperature). Add acetic anhydride (9000 ml) dropwise. When the addition is complete stir the reaction mixture for 1 hour at 45° C. and then stir overnight at room temperature. Concentrate the mixture under reduced pressure. Add ethyl acetate (20 L) and water (10 L) to the residue. Separate the organic layer and extract the aqueous layer with ethyl acetate (2×10 L). Combine the organic layers and wash with a saturated solution of citric acid (5 Kg) in water. Dry the organic layer over anhydrous sodium sulfate, filter, and concentrate under reduced pressure. Crystallise the residue from ethanol to give the title compound (3205.5 g; 92.11% yield): mass spectrum (m/z): 464.2 (M+1).

Method B

Scheme V, Step B: Wet D-glucose (517.30 mmoles; 93.20 g) with water (66 mL) and then add 4-methylindoline, (65.62 g; 492.67 mmoles) in ethanol (394 mL). Purge the mixture with nitrogen and heat to reflux under nitrogen atmosphere overnight. Then cool to room temperature and concentrate under reduced pressure. To the resulting residue, add dichloromethane (394 mL), triethylamine (2.82 moles; 393.72 mL), and N,N-dimethyl-4-pyridinamine, (24.63 mmoles; 3.01 g). Cool the mixture in an ice bath and then add acetic acid anhydride (3.94 moles; 372.57 mL) dropwise over 30 mins Concentrate the mixture under reduced pressure, dilute the residue with ethyl acetate (984 mL), and wash the mixture with citric acid (saturated aqueous solution; 50 mL) in water (200 mL). Separate the layers and extract the aqueous with ethyl acetate (600 mL then 300 mL). Combine the organics, wash with brine (600 mL), and concentrate under reduced pressure. Add ethanol (656 mL) and mix at 50° C. for 10 minutes. Cool the mixture to room temperature and then in ice/water. Filter the resulting mixture and dry under reduced pressure to give the title compound (112.2 g; 49.14% yield): mass spectrum (m/z): 464.2 (M+1).

Preparation 15

[2R,3R,4S,5R,6R)-3,4,5-triacetoxy-6-(4-methylindol-1-yl)tetrahydropyran-2-yl]methyl acetate

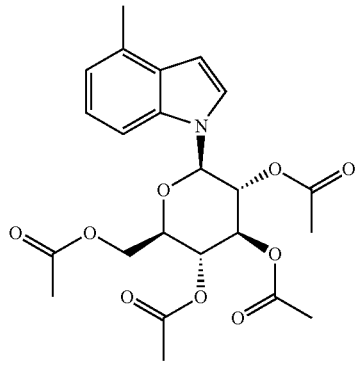 [SMILES: CC(=O)OC[C@H]1O[C@@H](n2ccc3c(C)cccc32)[C@H](OC(C)=O)[C@@H](OC(C)=O)[C@@H]1OC(C)=O]

Method A

Scheme V, Step C: Charge R2R,3R,4S,5R,6R)-3,4,5-triacetoxy-6-(4-methylindolin-1-yl)tetrahydropyran-2-yl]methyl acetate (4200 g; 9.08 moles) to a 20 L flask. Add 1,4 dioxane (42000 mL) and cool the solution to 10° C. Add DDQ (2057 g; 9.08 moles) in 5 equal portions maintaining the temperature at 10° C. After addition is complete, warm the mixture to room temperature and stir for 2 hours. Filter the reaction mixture and wash the solid with 1,4-dioxane (3 times). Concentrate the filtrate under reduced pressure and purify the residue by column chromatography eluting with 0%-20% ethyl acetate in hexane. Combine pure fractions with a separate lot of material prepared in a similar manner starting from 2500 g of [(2R,3R,4S,5R,6R)-3,4,5-triacetoxy-6-(4-methylindolin-1-yl)tetrahydropyran-2-yl]methyl acetate and concentrate under reduced pressure. Dissolve the residue in ethyl acetate (50L) and wash with a saturated solution of sodium bicarbonate (2×20 L) then water (1×10 L). Dry over anhydrous sodium sulphate, filter, concentrate under reduced pressure, and crystallize from ethanol (10 L) to give the title compound (4.632 Kg; 69% yield): mass spectrum (m/z): 462.5 (M+1).

Method B

Scheme V, Step C: Dissolve [(2R,3R,4S,5R,6R)-3,4,5-triacetoxy-6-(4-methylindolin-1-yl)tetrahydropyran-2-yl]methyl acetate (112.2 g; 242.08 mmoles) in 1,4-dioxane (1.68 L) at room temperature. Cool the mixture in an ice/water bath, then add 4,5-dichloro-3,6-dioxo-cyclohexa-1,4-diene-1,2-dicarbonitrile (244.50 mmoles; 55.50 g) portion-wise keeping the temperature of the reaction mixture below 15° C. When the addition is complete, stir the mixture for 5 minutes, then remove from the ice bath and stir for a further 5 minutes.

Filter the mixture and wash the solid with 1,4-dioxane (561.00 mL). Concentrate the filtrate under reduced pressure, then add ethanol (561.00 mL) to the residue, and stir at 40° C. for 20 minutes. Cool the mixture in ice water for 15 min, filter, and wash the solid obtained with cold ethanol (100 mL). Dry the solid under reduced pressure to give the title compound (82.5 g; 73.9% yield): mass spectrum (m/z): 462.0 (M+1).

Preparation 16

[(2R,3R,4S,5R,6R)-3,4,5-triacetoxy-6-[3-(4-bromobenzoyl)-4-methyl-indol-1-yl]tetrahydropyran-2-yl]methyl acetate

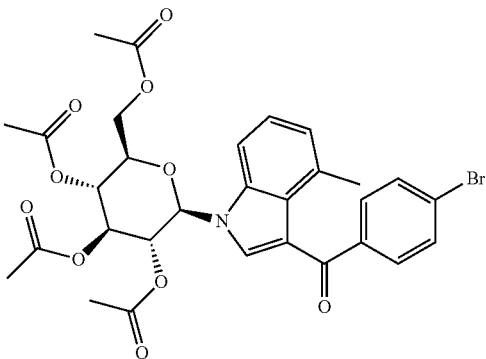 [SMILES: CC(=O)OC[C@H]1O[C@@H](n2cc(C(=O)c3ccc(Br)cc3)c3c(C)cccc32)[C@H](OC(C)=O)[C@@H](OC(C)=O)[C@@H]1OC(C)=O]

Scheme V, Step D: To a 20 L stirred reactor, purged with nitrogen, charge in order: aluminum trichloride (4.42 moles; 589.45 g) and dichloromethane (3.40 L). Cool the reactor jacket to 0° C., then allow the reaction mixture to cool below 10° C. Add 4-bromobenzoyl chloride (1.77 moles; 388.07 g) keeping the temperature below 10° C. Slowly add a solution of R2R,3R,4S,5R,6R)-3,4,5-triacetoxy-6-(4-methylindol-1-yl)tetrahydropyran-2-yl]methyl acetate (1.47 moles; 680.00 g) in dichloromethane (3.40 L) keeping temperature of the reaction mixture below 15° C. When the addition is complete, warm the reactor jacket to room temperature. After 8 hours, cool the reactor jacket to 4° C. and stir the mixture overnight. Cool the jacket to 0° C. and slowly pump the mixture into a second stirred vessel containing iced water (6.80 kg). After the addition is complete, allow the phases to separate. Concentrate the organic phase under reduced pressure. To the resulting residue, add MTBE (7.48 L) and wash with hydrochloric acid (0.5 M; 5.10 L), then water (7.48 L), and then sodium bicarbonate (5% w/w solution in water; 3.40 L). Filter the organic layer through a pad of diatomaceous earth (200 g), then concentrate the filtrate under reduced pressure. Dilute the residue with MTBE to give a total volume of 4000 mL, then add this solution with rapid stirring, at a rate of 35 ml/min to cold (0° C.) iso-hexane (13.60 L). When the addition is complete stir the mixture for 15 minutes, then filter. Allow the product to dry with air being sucked through the product cake overnight. Further dry the solid under reduced pressure to give the title compound in 63% purity as judged by LCMS (898.4 g; 59.60% yield): mass spectrum (m/z): 644.2/646.2 (M+1).

Preparation 17

[(2R,3R,4S,5R,6R)-3,4,5-triacetoxy-6-[3-R4-bromophenyl)-hydroxy-methyl]-4-methyl-indol-1-yl]tetrahydropyran-2-yl]methyl acetate

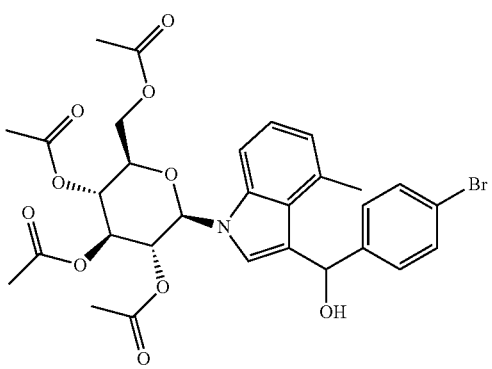 [SMILES: CC(=O)OC[C@H]1O[C@@H](n2cc(C(O)c3ccc(Br)cc3)c3c(C)cccc32)[C@H](OC(C)=O)[C@@H](OC(C)=O)[C@@H]1OC(C)=O]

Scheme V, Step E: To a 20 L stirred reactor, purged with nitrogen, charge sodium tetrahydroborate (2.15 moles; 81.36 g), then tetrahydrofuran (3.50 L). Set the reactor jacket to 0° C., and when the reaction mixture is 2° C., charge cerium (III) chloride heptahydrate (2.15 moles; 530 g). Add slowly a solution of [(2R,3R,4S,5R,6R)-3,4,5-triacetoxy-6-[3-(4-bromobenzoyl)-4-methyl-indol-1-yl]tetrahydropyran-2-yl]methyl acetate (716.86 mmoles; 700.00 g) in tetrahydrofuran (3.01 L) not allowing the temperature of the reaction mixture to exceed 10° C. Add a mixture of tetrahydrofuran (504.00 mL) and ethanol (504.00 mL) slowly, then add ethanol (504.00 mL) slowly with the reaction mixture temperature not exceeding 10° C. (Note: both additions of ethanol must be done slowly and with care as a latent exotherm may be seen). Stir the mixture for 10 minutes. To a separate vessel, charge hydrochloric acid (2M; 7.00 L), water (10.5 L), and ice (10.5 Kg), then slowly pump the reaction mixture into the cold hydrochloric acid mixture. Extract the mixture with ethyl acetate (5.07 L then 2.66 L) and combine the organic extracts. Wash the combined organic extracts with sodium bicarbonate (5% w/v aqueous solution; 3.50 L) then sodium chloride (10% w/v aqueous solution; 3.50 L), dry over anhydrous magnesium sulphate, and concentrate under reduced pressure. Dissolve the resulting residue in MTBE(1.00 L) and concentrated under reduced pressure to give the title compound as a mixture of diastereomers in sufficient purity to be used without further purification in the next step: mass spectrum (m/z): 628.2/630.2 (M+1-18).

Preparation 18

[(2R,3R,4S,5R,6R)-3,4,5-triacetoxy-6-[3-[(4-bromophenyl)methyl]-4-methyl-indol-1-yl]tetrahydropyran-2-yl[methyl acetate

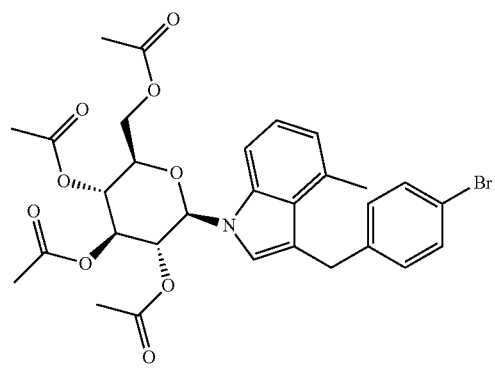 [SMILES: CC(=O)OC[C@H]1O[C@@H](n2cc(Cc3ccc(Br)cc3)c3c(C)cccc32)[C@H](OC(C)=O)[C@@H](OC(C)=O)[C@@H]1OC(C)=O]

Scheme V, Step F: To a 20 L temperature controlled reactor charge [(2R,3R,4S,5R,6R)-3,4,5-triacetoxy-6-[3-[(4-bromophenyl)-hydroxy-methyl]-4-methyl-indol-1-yl]tetrahydropyran-2-yl]methyl acetate (1492.5 g; 65% purity; 1.506 moles), then acetonitrile (4.87 L), and then dichloromethane (4.87 L). Cool the mixture to 0° C. Add triethylsilane (3.77 moles; 437.83 g) over 5 minutes. Set the reactor jacket to −5° C. When the reaction mixture temperature is −2° C., start addition of boron trifluoride etherate (3.77 moles; 534.4 g). Note: at the start, this addition results in a significant exotherm (temperature increases to ~8° C. during the first ~10 ml of addition). Once the initial exothermic event has taken place, add the remainder of the boron trifluoride etherate at a rate to maintain the temperature between 5° C. and 7° C. When the addition is complete stir the reaction mixture at 5° C. for 50 minutes. Charge a 50 L glass flask equipped with a bottom outlet valve with ice (6 kg), and then water (~15 C; 3.74 Kg). Add sodium bicarbonate (11.16 moles; 937.55 g) and stir the mixture for 5 minutes. Pump the reaction mixture into the sodium bicarbonate mixture over about 5 minutes. A little effervescence is seen, but no tendency to foam. Add ethyl acetate (17.04 L) and stir the mixture for 10 minutes. Stop the stiffing and allow the mixture to stand for 30 minutes. Separate the layers, wash the organic phase with brine (4.87 L), and concentrate under reduced pressure. Split the mixture into two approximately equal portions and purify each by passage through a 4.5 Kg pad of silica eluting with dichloromethane. Concentrate the appropriate fractions to give the title compound (990 g, about 70% purity (as determined by quantative NMR; 73% yield from [(2R,3R,4S,5R,6R)-3,4,5-triacetoxy-6-[3-(4-bromobenzoyl)-4-methyl-indol-1-yl]tetrahydropyran-2-yl]methyl acetate): mass spectrum (m/z): 630.2/632.2 (M+1).

Preparation 19 tert-butyl 4-[(E)-4-[4-[[4-methyl-1-[(2R,3R,4S,5R,6R)-3,4,5-triacetoxy-6-(acetoxymethyl)tetrahydropyran-2-yl]indol-3-yl]methyl]phenyl]but-3-enyl]-4,9-diazaspiro[5.5]undecane-9-carboxylate

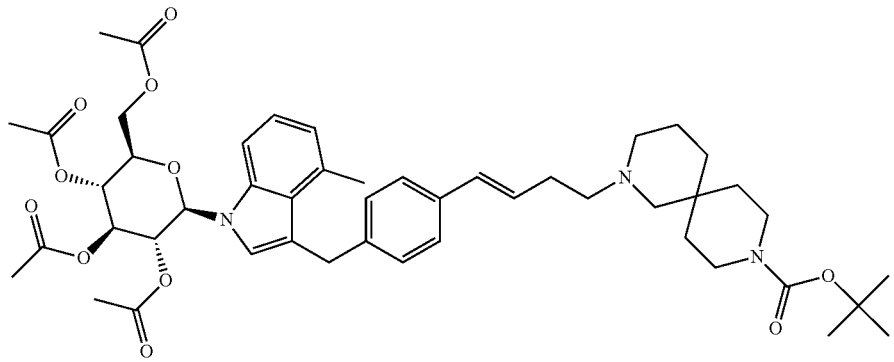 [SMILES: CC(=O)OC[C@H]1O[C@@H](n2cc(Cc3ccc(/C=C/CCN4CCCC5(CCN(C(=O)OC(C)(C)C)CC5)C4)cc3)c3c(C)cccc32)[C@H](OC(C)=O)[C@@H](OC(C)=O)[C@@H]1OC(C)=O]

Scheme V, Step G: To a 20 L temperature controlled reactor charge [(2R,3R,4S,5R,6R)-3,4,5-triacetoxy-6-[3-[(4-bromophenyl)methyl]-4-methyl-indol-1-yl]tetrahydropyran-2-yl]methyl acetate (1.37 moles; 1.18 kg; 73% purity), tert-butyl 8-[(E)-4-(4,4,5,5-tetramethyl-1,3,2-dioxaborolan-2-yl)but-3-enyl]-3,8-diazaspiro[5.5]undecane-3-carboxylate (1.79 moles; 776.46 g), potassium carbonate (3.85 moles; 532.03 g), THF (11.80 L) and water (1.18 L). Degas the mixture by subsurface nitrogen purge for 30 minutes and then add Pd(OAc)₂ (54.99 mmoles; 12.35 g) and XPhos (54.99 mmoles; 26.22 g). Heat the mixture to 65° C. and stir overnight. Charge additional XPhos (13.75 mmoles; 6.55 g) and Pd(OAc)₂ (13.75 mmoles; 3.09 g) and continue to stir at 65° C. for about 1 hour. Prepare a solution of tert-butyl 8-[(E)-4-(4,4,5,5-tetramethyl-1,3,2-dioxaborolan-2-yl)but-3-enyl]-3,8-diazaspiro[5.5]undecane-3-carboxylate (343.71 mmoles; 149.32 g) in THF (500 mL) and degas by subsurface purge with nitrogen for 5 mins. Add this solution to the main reaction mixture and continue stirring at 65° C. for about 3 hours. Cool the reaction mixture to room temperature and pump into a 50 L vessel equipped with a bottom outlet valve. Dilute the mixture with iso-hexane (11.80 L) and wash with brine (11.80 L). Separate the layers and filter the organic phase through a pad of silica gel (2.95 kg). Wash the pad twice with a mixture of THF (5.90 L) and iso-hexane (5.90 L). Concentrate the filtrate under reduced pressure to give the title compound (1.695 Kg; 62% purity as judged by quantative NMR; 88% yield), mass spectrum (m/z): 858.4 (M+1).

Preparation 20

[(2R,3R,4S,5R,6R)-3,4,5-triacetoxy-6-[3-[[4-[(E)-4-(4,9-diazoniaspiro[5.5]undecan-4-yl)but-1-enyl[phenyl]methyl]-4-methyl-indol-1-yl]tetrahydropyran-2-yl]methyl acetate dihydrochloride

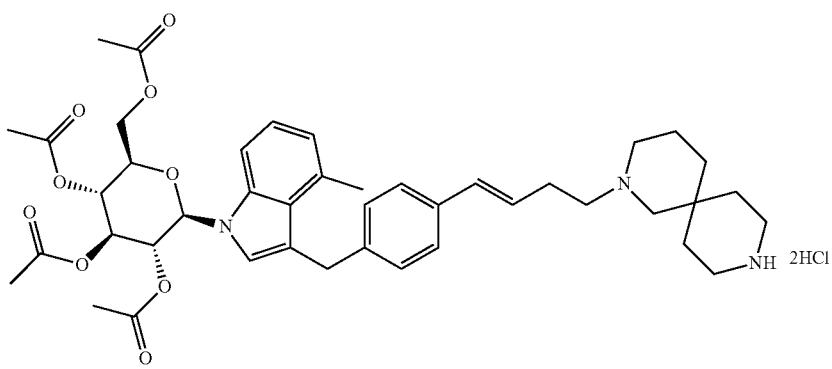 [SMILES: CC(=O)OC[C@H]1O[C@@H](n2cc(Cc3ccc(/C=C/CCN4CCCC5(CCNCC5)C4)cc3)c3c(C)cccc32)[C@H](OC(C)=O)[C@@H](OC(C)=O)[C@@H]1OC(C)=O]

Scheme V, Step H: Dissolve tert-butyl 4-[(E)-4-[4-[[4-methyl-1-[(2R,3R,4S,5R,6R)-3,4,5-triacetoxy-6-(acetoxymethyl)tetrahydropyran-2-yl]indol-3-yl]methyl]phenyl]but-3-enyl]-4,9-diazaspiro5.5]undecane-9-carboxylate (1.22 moles; 1.68 kg) in dichloromethane (8.36 L) and add hydrogen chloride (4M in dioxane; 8.52 moles; 2.13 L) keeping the reaction below 30° C. Stir the reaction at room temperature overnight. Concentrate the mixture under reduced pressure. To the residue add dichloromethane (1.04 L) with stiffring. Add the resulting solution slowly to MTBE (10.45 L) with stirring. Collect the resulting solid by filtration and wash the cake with MTBE (2 L). Dry the solid under reduced pressure to give the title compound (1.49 kg, 66% purity; 97.19% yield): mass spectrum (m/z): 758.4 [M(freebase)+1].

Example 1c

Alternative synthesis of 1-isobutyl-3-[2-[4-[(E)-4-[4-[[4-methyl-1-[(2R,3R,4S,5S,6R)-3,4,5-trihydroxy-6-(hydroxymethyl)tetrahydropyran-2-yl]indol-3-yl]methyl]phenyl]but-3-enyl[-4,9-diazaspiro[5.5]undecan-9-yl]-2-oxo-ethyl]urea

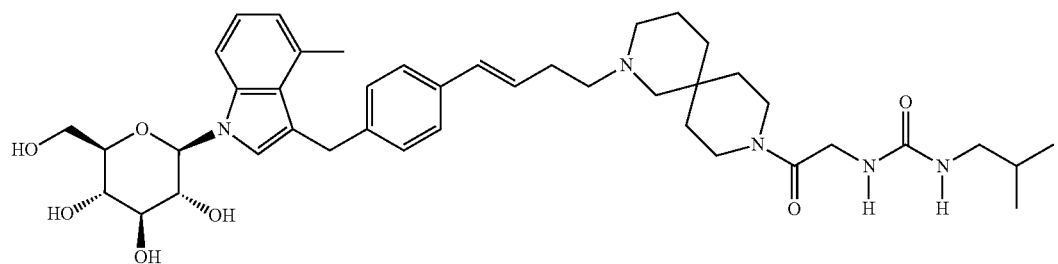 [SMILES: Cc1cccc2c1c(Cc1ccc(/C=C/CCN3CCCC4(CCN(C(=O)CNC(=O)NCC(C)C)CC4)C3)cc1)cn2[C@@H]1O[C@H](CO)[C@@H](O)[C@H](O)[C@H]1O]

Scheme V, Step I: To a 10 L reactor with jacket set at 25° C. add: R2R,3R,4S,5R,6R)-3,4,5-triacetoxy-6-[3-[[4-[(E)-4-(4,9-diazoniaspiro[5.5]undecan-4-yl)but-1-enyl]phenyl]methyl]-4-methyl-indol-1-yl]tetrahydropyran-2-yl]methyl acetate dihydrochloride (782.34 mmoles; 650.0 g), dichloromethane (2.35 L), and then triethylamine (3.91 moles; 545.22 mL). Stir the mixture for 10 minutes. Label this reactor A. Charge a separate 20 L flask with 2-(isobutylcarbamoylamino)acetic acid (899.69 mmoles; 183.30 g) and dichloromethane (2.35 L), and then add 1,1'-carbonyldiimidazole (938.80 mmoles; 152.23 g) over 1 minute. Note: There is some gas evolution on addition of CDI. Stir the mixture for 5 minutes. Label this reactor B. Pump the mixture in reactor B into reactor A at a rate of ~3800 mL/min. Stir the reaction at room temperature for about 2 hours. To a clean flask add 2-(isobutylcarbamoylamino)acetic acid (89.97 mmoles; 18.33 g) and dichloromethane (234.7 mL) and then 1,1'-carbonyldiimidazole (93.88 mmoles; 15.22 g). Stir the mixture for 5 minutes and then add to reactor A. Stir the mixture for about 10 minutes. Pump the reaction mixture into water (5.04 L) and stir. Stop the stirring, separate the organic phase, and concentrate under reduced pressure. Dissolve the residue in methanol (38.66 moles; 1.56 L; 1.24 kg) and add sodium methoxide (25% w/w in MeOH; 1.56 moles; 352.21 mL) over 10 minutes. Stir the mixture for 30 minutes. Concentrate the reaction mixture under reduced pressure. Dissolve the residue in methanol (250.00 mL) and add dichloromethane (1.50 L). Add the solution to rapidly stirred MTBE (10.00 L) over 5 mins Filter the resulting suspension and air dry overnight. Dissolve the solid in 20% MeOH in dichloromethane (5 L) and pass through a 6 Kg silica pad eluting with 15% v/v MeOH in dichloromethane. Combine the appropriate fractions and concentrate under reduced pressure. Further purify the residue by flash chromatography (C18 column) eluting with 25-80% acetonitrile in aqueous ammonium hydrogen carbonate (10 mM) then combine the appropriate fractions to give the title compound; $[\alpha]_D^{20} = 6.6°$ (C=0.976, methanol).

Sodium-Dependent Glucose Transporter 1 (SGLT1) Assays

The cDNA encoding human SGLT1 (slc5a1, NM_000343) and mouse SGLT1 (slc5a1, NM_019810.4) are purchased from Openbiosystems. The cDNA is cloned into pcDNA3.1+ for mammalian expression and is stably transfected into Chinese hamster ovary (CHO)-K1 cells using standard mammalian transfection procedures. An SGLT-expressing sub-clone of each over-expressing cell line is selected based on resistance to neomycin (Geneticin, Invitrogen) and activity in the $^{14}$C-a-methyl-D-glucopyranoside ($^{14}$C-AMG) uptake assay (see below). Stable SGLT-expressing cells are maintained using standard cell culture techniques.

The SGLT activity is measured as sodium-dependent $^{14}$C-AMG uptake in the above cell lines described as follows. One hundred mL of culture medium containing 30,000 cells are seeded to each well of a 96-well BioCoat poly-D-lysine plate (Becton Dickson) and cultured at 37° C. overnight. The culture medium is aspirated and cells are washed twice with 200 mL of Reaction Buffer (140 mM NaCl, 2 mM KCl, 1 mM $CaCl_2$, $MgCl_2$, and 14 mM N-2-hydroethylpiperrazine-N'-2-ethanesulfonic acid (Hepes), pH 7.5). The excess buffer is tapped out onto paper towels. Thirty-five mL of Reaction Buffer are added to each well. Five mL of a 10% dimethylsufoxide (DMSO) in Reaction Buffer containing varying concentrations of test compound or no compound as a control, is dispensed into the each well. The reaction is initiated by adding 10 mL of $^{14}$C-AMG in Reaction Buffer to make a final concentration of 4 mM. The plate is incubated at 37° C. for 125 minutes. The reaction is terminated by aspirating off Reaction Buffer and then washed three times with 200 mL of ice cold Reaction Buffer. Manual aspiration is applied to ensure the complete removal of Reaction Buffer. Ten mL of 0.1 N NaOH is added to each well and then 100 mL of Supermix scintillation cocktail (PerkinElmer) is added. After mixing, the scintillation signal in the plate is counted in a MicroBeta (PerkinElmer). A ten-dose response curve is fitted to an empirical four-parameter model using ActivityBase (ID Business Solution) to determine the inhibitor concentration at half-maximal inhibition ($IC_{50}$).

The compound of Example 1 herein is tested essentially as described above and exhibits an IC$_{50}$ for human SGLT1 of 17.4±14.6 nM (n=9) and an IC$_{50}$ for mouse SGLT1 of 13.6±7.3 nM (n=6). These data demonstrate that the compound of Example 1 inhibits human and mouse SGLT1 in vitro.

Glucose Lowering Effects in Oral Glucose Tolerance Test (OGTT)

The test compound is formulated by adding a vehicle of 1% hydroxyethylcellulose, 0.25% Tween® 80 w/antifoam 0.05% to preweighed test compound to make a 1 mg/ml solution. The mixture is probe sonicated for approximately 1 minute. A stir bar is added, and the resulting suspension is stirred continuously throughout dosing.

One of two sets of single housed C57B1/6 mice are weighed and body weights used to determine study groups (n=5), within a working range of 26-30 g. After grouping, the mice are orally gavaged with 10 ml/kg test compound preparation or vehicle, thirty seconds apart. These mice are used to demonstrate the compound's effects in an OGTT, 18 hours later. Both sets of mice are then fasted overnight by removing access to food, late afternoon before test day. The following morning, the remaining mice, are weighed and bled (via tail snip) for glucose. Study groups (n=5) are determined using fasted glucose values, within a working range of 80-100 mg/dl. After grouping, the mice are orally gavaged using the same protocol as the previous day.

At eight and eighteen hours after each respective compound treatment is started, a baseline blood sample is taken for measuring glucose (from the first animal). The animal is then immediately given an oral dose of 50% dextrose (Hospira®) at 3 g/kg. Blood samples are taken for glucose, exactly thirty seconds apart, by tail vein so that blood is collected in each animal at 20, 40 and 60 minutes after the dextrose dose.

TABLE 1

Glucose lowering effects in OGTT.
Oral Glucose Tolerance Test Results Mean ± SEM
1 way ANOVA/Dunnett's compared to vehicle *p < 0.05, **p < 0.01

|  | Vehicle @ 8 hrs post dose | Example 1 10 mg/kg @ 8 hrs post dose | Vehicle @ 18 hrs post dose | Example 1 10 mg/kg @ 18 hrs post dose |
|---|---|---|---|---|
| | Glucose (mg/dl) | | | |
| 0 Minute | 72.10 ± 5.47 | 70.2 ± 5.47 | 79.0 ± 1.17 | 87.7 ± 3.36 |
| 20 Minute | 327.9 ± 39.1 | 119.1 ± 11.4** | 257.8 ± 19.1 | 116.1 ± 2.71** |
| 40 Minute | 271.1 ± 47.7 | 127.7 ± 8.32** | 202.8 ± 5.38 | 130.7 ± 4.47** |
| 60 Minute | 176.5 ± 11.8 | 132.6 ± 8.85* | 154.7 ± 5.32 | 124.1 ± 1.42** |

TABLE 1-continued

Glucose lowering effects in OGTT.
Oral Glucose Tolerance Test Results Mean ± SEM
1 way ANOVA/Dunnett's compared to vehicle *p < 0.05, **p < 0.01

|  | Vehicle @ 8 hrs post dose | Example 1 10 mg/kg @ 8 hrs post dose | Vehicle @ 18 hrs post dose | Example 1 10 mg/kg @ 18 hrs post dose |
|---|---|---|---|---|
| Baseline Adjusted AUC | 10140 ± 1662 | 2752 ± 507** | 6809 ± 419 | 1792 ± 254** |
| | Glucose (mg/dl) | | | |
| Glucose Cmax | 334.7 ± 40.9 | 134.7 ± 8.31** | 261 ± 16.3 | 132.7 ± 3.27** |
| | Time (minutes) | | | |
| Glucose Tmax | 24 ± 4 | 48 ± 8* | 24 ± 4 | 48 ± 4.9 |

As shown in table 1, the compound of Example 1 delivers a decrease in the glucose excursion when an oral bolus of 50% dextrose (Hospira®) is given to a normal glycemic C57B1/6 mouse eight or eighteen hours after administration. Example 1 also demonstrates a decrease in baseline adjusted glucose area under the curve (AUC) during both OGTTs. In addition, Example 1 decreases the average maximum concentration of plasma glucose (Cmax) during the OGTTs while increasing the average time that it takes for glucose to reach maximum concentration (Tmax).

I claim:

1. A compound of the formula:

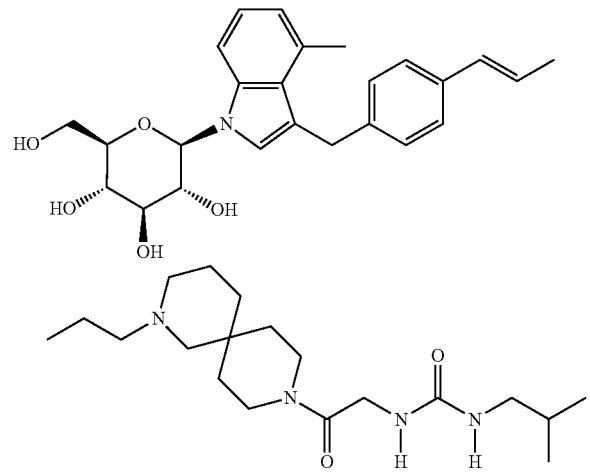

or a pharmaceutically acceptable salt thereof.

2. The compound according to claim 1 which is:

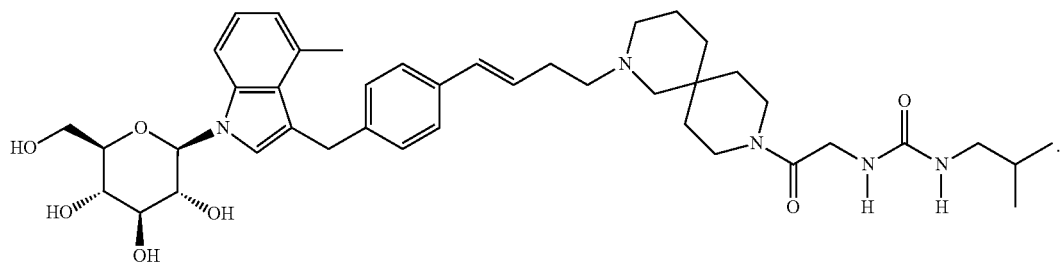 [SMILES: Cc1cccc2c1c(Cc1ccc(/C=C/CCN3CCCC4(CCN(C(=O)CNC(=O)NCC(C)C)CC4)C3)cc1)cn2[C@@H]1O[C@H](CO)[C@@H](O)[C@H](O)[C@H]1O]

3. A method of treating diabetes in a patient comprising administering to a patient in need of such treatment an effective amount of a compound, or pharmaceutically acceptable salt thereof, according to claim 1.

4. A method of treating type 1 diabetes in a patient comprising administering to a patient in need of such treatment an effective amount of a compound, or pharmaceutically acceptable salt thereof, according to claim 1.

5. A method of treating type 2 diabetes in a patient comprising administering to a patient in need of such treatment an effective amount of a compound, or pharmaceutically acceptable salt thereof, according to claim 1.

6. A pharmaceutical composition comprising a compound or salt according to claim 1 with one or more pharmaceutically acceptable carriers, diluents, or excipients.

\* \* \* \* \*